(12) United States Patent
Melsky et al.

(10) Patent No.: US 10,926,067 B2
(45) Date of Patent: Feb. 23, 2021

(54) BALLOON CATHETER AND FLUID MANAGEMENT SYSTEM THEREOF

(71) Applicant: CardioFocus, Inc., Marlborough, MA (US)

(72) Inventors: Gerald Melsky, Lexington, MA (US); Brian Estabrook, Foxboro, MA (US); Lincoln Baxter, Centerville, MA (US); Sergei Babko-Malyi, Winchester, MA (US); Ronald Green, Bethel, CT (US); Paul DiCeare, Marlborough, MA (US); Richard Clark, Marlborough, MA (US); Richard Thompson, Marlborough, MA (US); Michael Magill, Marlborough, MA (US); Burke Barrett, Marlborough, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 574 days.

(21) Appl. No.: 15/863,373

(22) Filed: Jan. 5, 2018

(65) Prior Publication Data
US 2018/0193613 A1  Jul. 12, 2018

Related U.S. Application Data

(60) Provisional application No. 62/485,691, filed on Apr. 14, 2017, provisional application No. 62/443,270, filed on Jan. 6, 2017.

(51) Int. Cl.
*A61M 25/10* (2013.01)
*A61M 39/22* (2006.01)
(Continued)

(52) U.S. Cl.
CPC ....... *A61M 25/10185* (2013.11); *A61B 18/00* (2013.01); *A61B 18/1492* (2013.01); *A61M 25/10187* (2013.11); *A61M 39/223* (2013.01); *A61B 2018/0022* (2013.01); *A61B 2018/00023* (2013.01); *A61B 2018/00577* (2013.01); *A61B 2018/00982* (2013.01); *A61B 2090/3614* (2016.02); *A61M 2025/0003* (2013.01)

(58) Field of Classification Search
CPC combination set(s) only.
See application file for complete search history.

(56) References Cited

U.S. PATENT DOCUMENTS

2003/0229264 A1   12/2003  Connors et al.
2004/0111138 A1    6/2004  Bleam et al.
(Continued)

*Primary Examiner* — Scott Luan
(74) *Attorney, Agent, or Firm* — Leason Ellis LLP

(57) ABSTRACT

Systems and methods for controlling fill media in a balloon catheter are disclosed. The system comprises a catheter having an inflatable balloon, a reservoir for fill media, and a first conduit for delivering fill media from the reservoir to the balloon. The system includes a second conduit for returning fill media from the balloon to the reservoir and a pump configured to circulate fill media through the conduits. The system also includes a valve assembly configured for placement in at least three positions. In the first position, fill media is delivered from the reservoir to the balloon to inflate the balloon. In the second position, fill media is drawn out of the balloon and returned to the reservoir. In the third position, fill media circulates through the conduits between the pump and the balloon and is prevented from flowing back to the reservoir.

15 Claims, 38 Drawing Sheets

(51) Int. Cl.
*A61B 18/00* (2006.01)
*A61B 18/14* (2006.01)
A61M 25/00 (2006.01)
A61B 90/00 (2016.01)

(56) References Cited

U.S. PATENT DOCUMENTS

| | | |
|---|---|---|
| 2005/0209662 A1 | 9/2005 | Lunderqvist et al. |
| 2011/0202084 A1 | 8/2011 | Hoem et al. |
| 2013/0079737 A1 | 3/2013 | Hanuka et al. |
| 2014/0121515 A1 | 5/2014 | Vitullo et al. |

# BALLOON CATHETER AND FLUID MANAGEMENT SYSTEM THEREOF

CROSS REFERENCE TO RELATED APPLICATIONS

The present application claims priority to U.S. patent application Ser. No. 62/485,691, filed on Apr. 14, 2017, which is hereby incorporated by reference in its entirety and the present application is related to U.S. patent application Ser. No. 62/443,270, filed Jan. 6, 2017, which is hereby incorporated by reference in its entirety.

FIELD OF INVENTION

The present invention relates to balloon catheters used to treat atrial fibrillation and other medical conditions. In particular, the present invention relates to systems and methods for controlling fill media in the balloon catheter.

BACKGROUND

Balloon catheters can be used for a variety of medical procedures, including in the treatment of atrial fibrillation. In certain types of balloon catheters, a fill media is used to inflate the balloon and maintain the balloon at the inflated state while the procedure is performed. Once the balloon has been inflated to the desired size and pressure, the balloon fill media is circulated into and out of the balloon to keep the balloon temperature cool such that it does not damage the tissue of the patient. Conventionally, balloon catheters have been filled to pressures of 2 to 5 PSI. However, some balloon catheters now have lower pressures which allow for the balloon catheter to achieve greater contact with the patient's tissue. The prior art methods for cooling the balloon, however, are not compatible with balloons having a lower PSI. In particular, achieving the desired lower PSI using the prior art systems would require a lower flow rate of the fill media; however, this lower flow rate of the fill media is not adequate to keep the balloon and catheter components cool.

Additionally, in conventional designs, the operator/manipulator (e.g., physician) of the balloon catheter in the body of the patient relies on a separate, remote operator to inflate (or deflate) the balloon catheter to the desired size and pressure. As such, at least two operators are required in order to perform a medical procedure using the balloon catheter, as the operator who manipulates the balloon in the body of the patient must rely on a separator operator to inflate or deflate the balloon catheter.

Accordingly, the present systems and methods address these and other problems associated with balloon catheters.

SUMMARY

The present application relates to systems and methods for controlling fill media in the balloon catheter.

In a first aspect, a balloon catheter system is disclosed. The system comprises a balloon catheter, which includes a catheter body and an inflatable balloon coupled to one end of the body. The system further comprises a fluid management system for controllably inflating and deflating the balloon. The fluid management system includes a reservoir for storing balloon fill media, and a first conduit connected between the reservoir and the balloon for delivering the balloon fill media. The fluid management system further includes a second conduit connected between the balloon and the reservoir for returning the balloon fill media from the balloon to the reservoir, and a pump disposed along the first conduit. The pump is configured to circulate the balloon fill media along a circuit defined by the first and second conduits. The fluid management system also includes a valve assembly disposed along the first and second conduits, with the pump being disposed along the first conduit between the valve assembly and the balloon. The valve assembly is configured for placement in at least a first position, a second position, and a third position. In the first position, the balloon fill media is delivered from the reservoir and pumped into the balloon for inflation of the balloon. In the second position, the balloon fill media is drawn out of the balloon and pumped back to the reservoir. In the third position, the balloon fill media circulates from the pump through the first conduit to the balloon and through the second conduit from the balloon back to the pump and is prevented from flowing back to the reservoir from the balloon.

These and other aspects, features, and advantages can be appreciated from the accompanying description of certain embodiments of the invention and the accompanying drawing figures and claims.

BRIEF DESCRIPTION OF THE DRAWING FIGURES

FIG. 1 displays a schematic of a balloon fill media control system in a trapped volume state in accordance with one or more embodiments;

FIG. 2 displays a schematic of the balloon fill media control system in an inflate state in accordance with one or more embodiments;

FIG. 3 displays a schematic of the balloon fill media control system in an deflate state in accordance with one or more embodiments;

FIG. 4 displays a side perspective view of an implementation of the balloon fill media control system having a rocker valve assembly in accordance with one or more embodiments;

FIG. 5 displays a cross section of the rocker valve assembly in accordance with one or more embodiments;

FIG. 6 displays a side perspective view of an implementation of the balloon fill media control system having a rocker valve assembly in the trapped volume mode in accordance with one or more embodiments;

FIG. 7 displays a side perspective view of an implementation of the balloon fill media control system having a rocker valve assembly in the inflate mode in accordance with one or more embodiments;

FIG. 8 displays a side perspective view of an implementation of the balloon fill media control system having a rocker valve assembly in the deflate mode in accordance with one or more embodiments;

FIG. 9 displays a top perspective view of an exemplary valve housing body of the rocker valve assembly in accordance with one or more embodiments;

FIG. 10 displays another top perspective view of the exemplary valve housing body of the rocker valve assembly in accordance with one or more embodiments;

Figure 24:
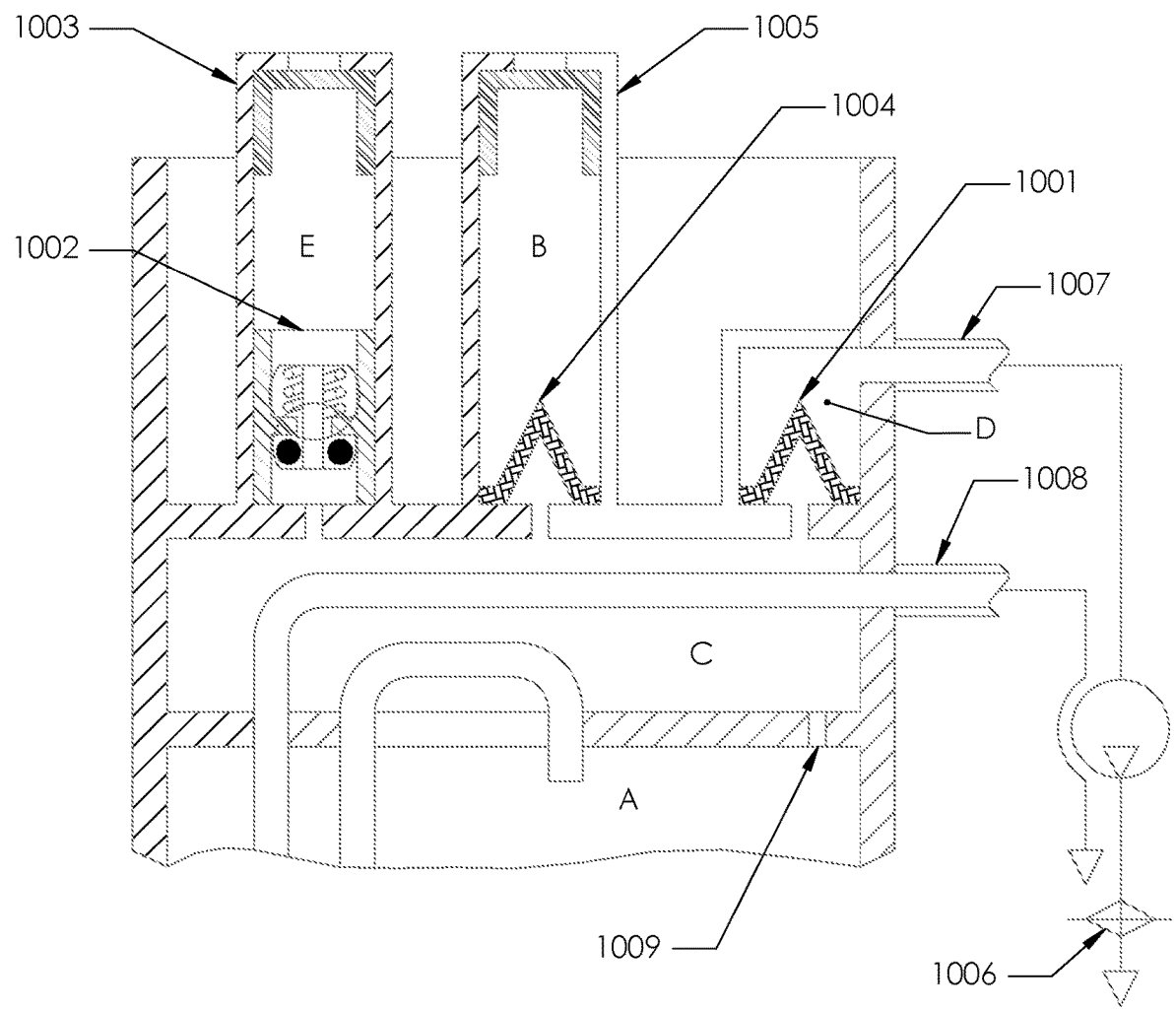
Figure 25:
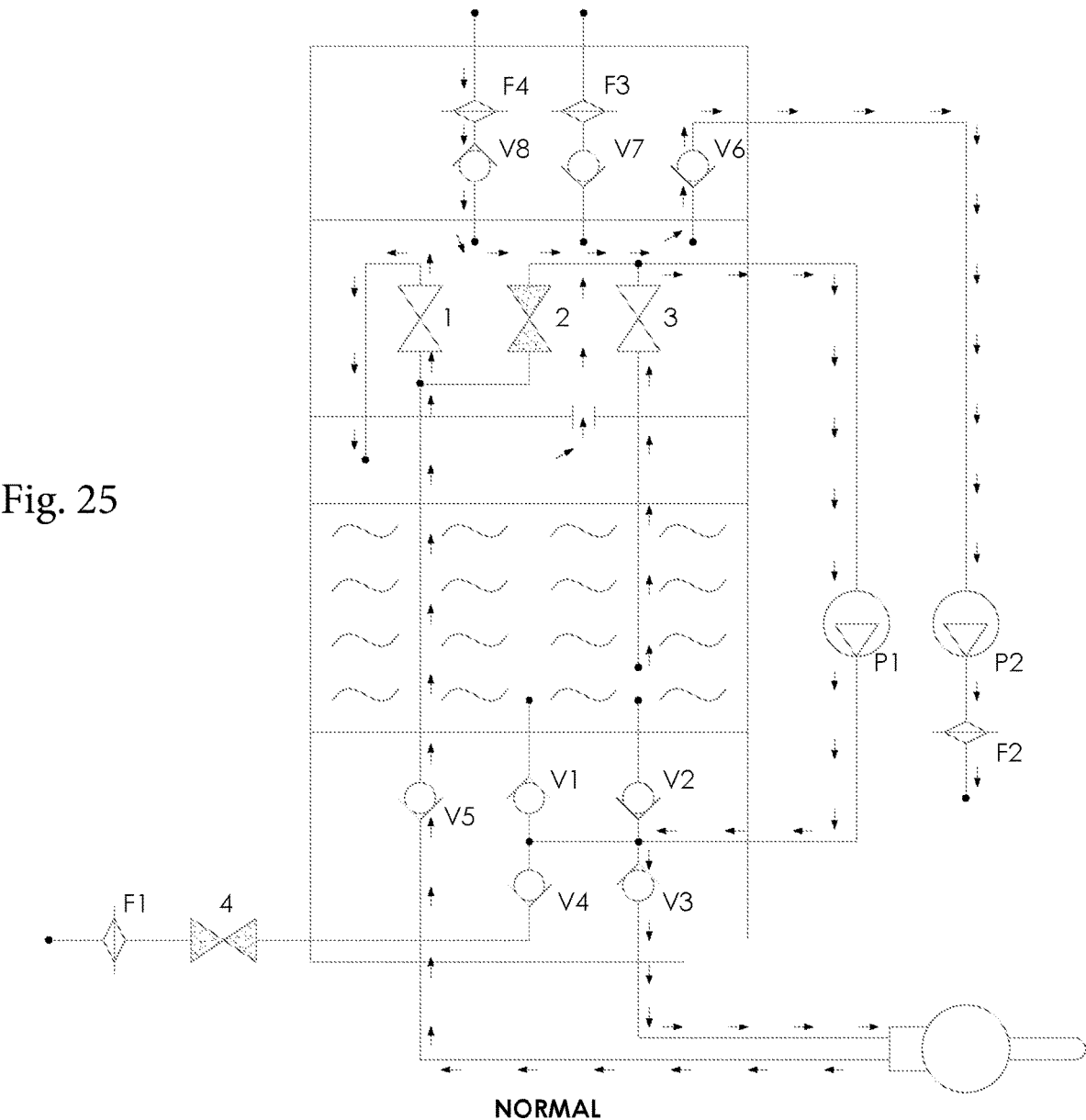
Figure 26:
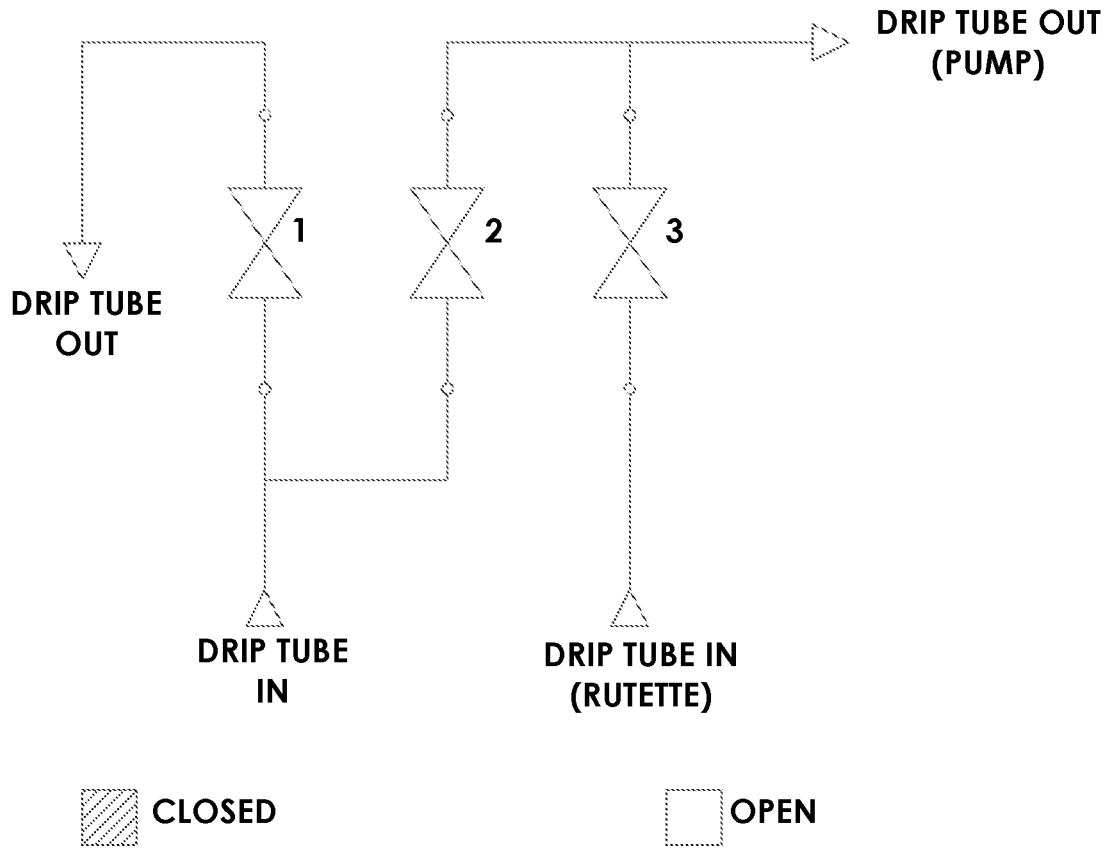
Figure 27:
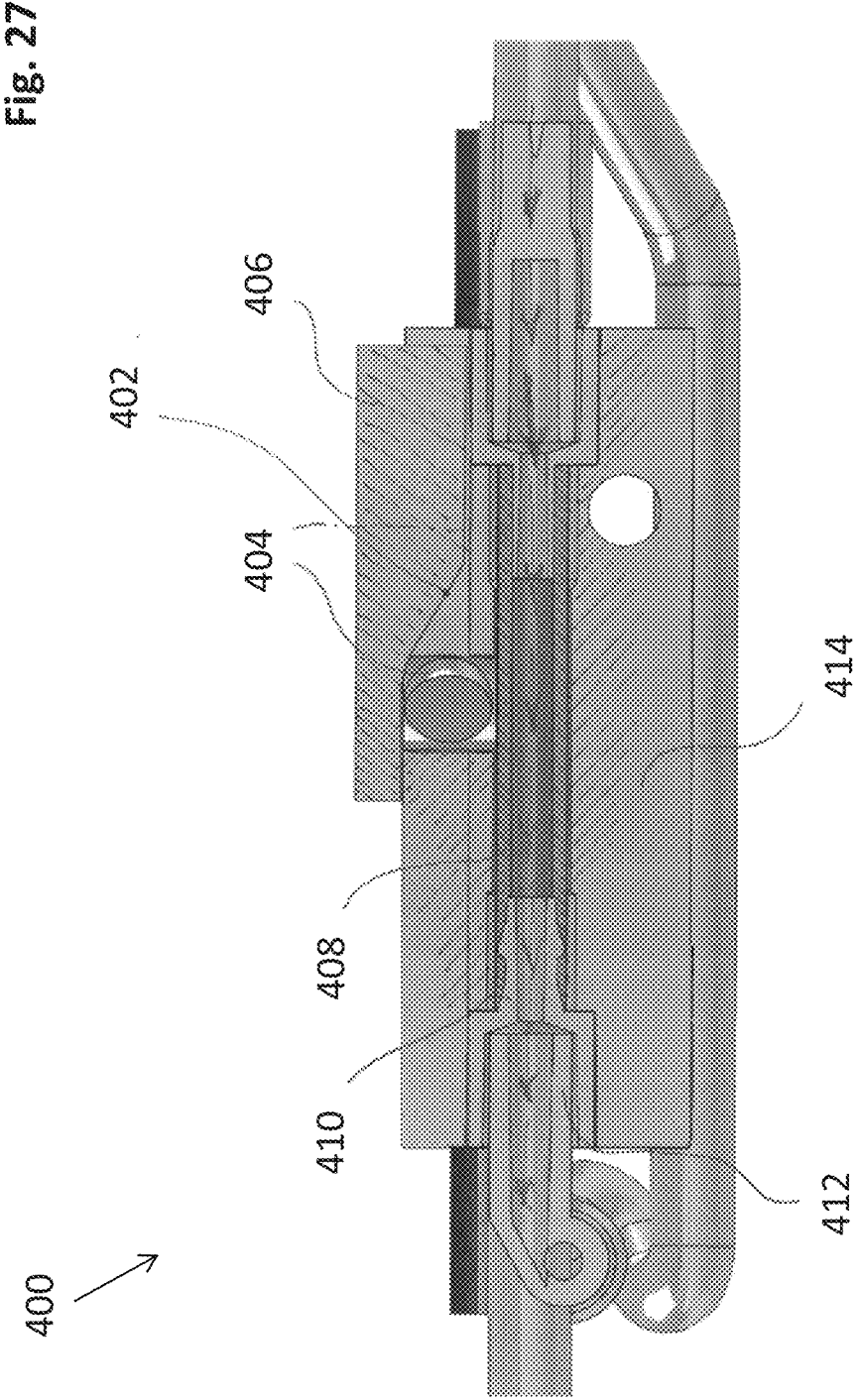
Figure 28:
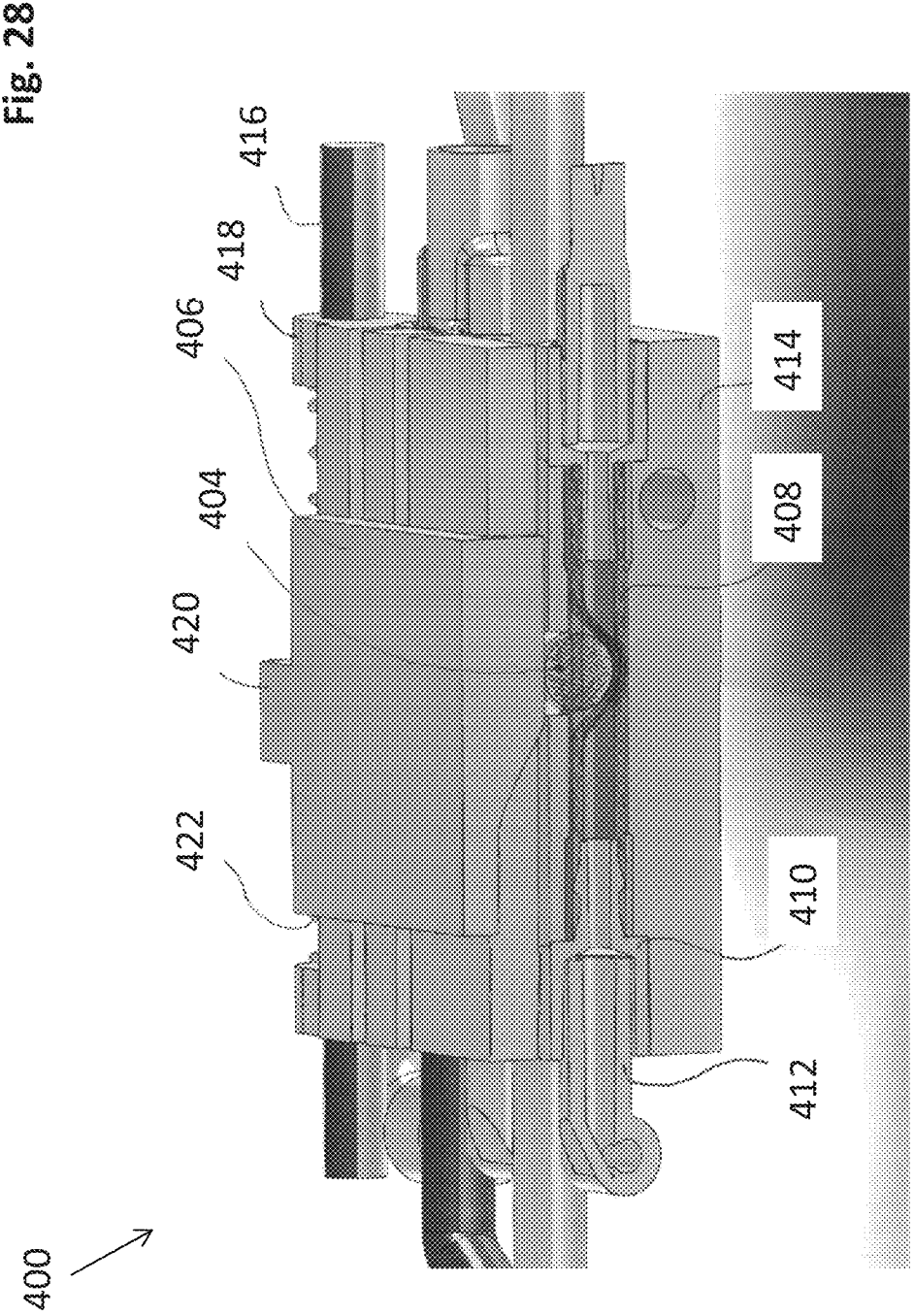
Figure 29:
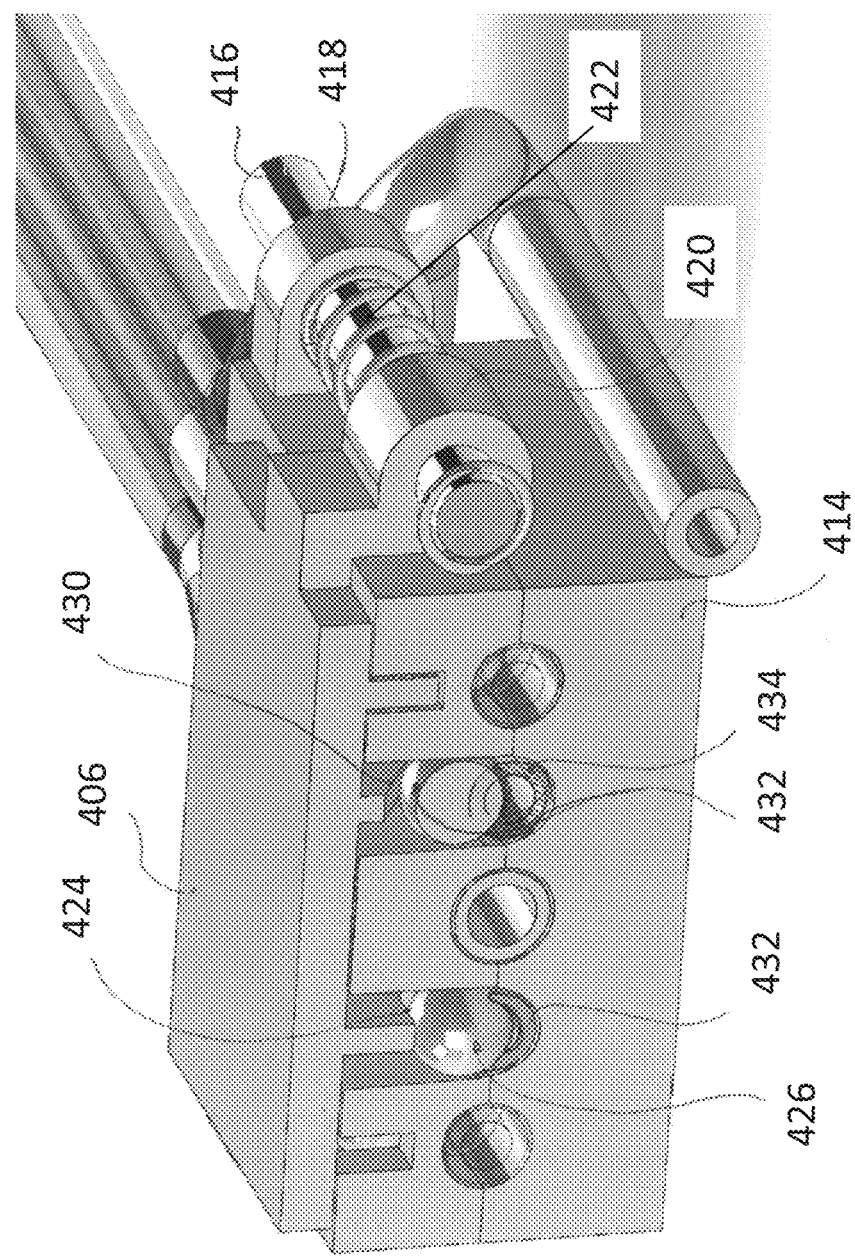
Figure 30:
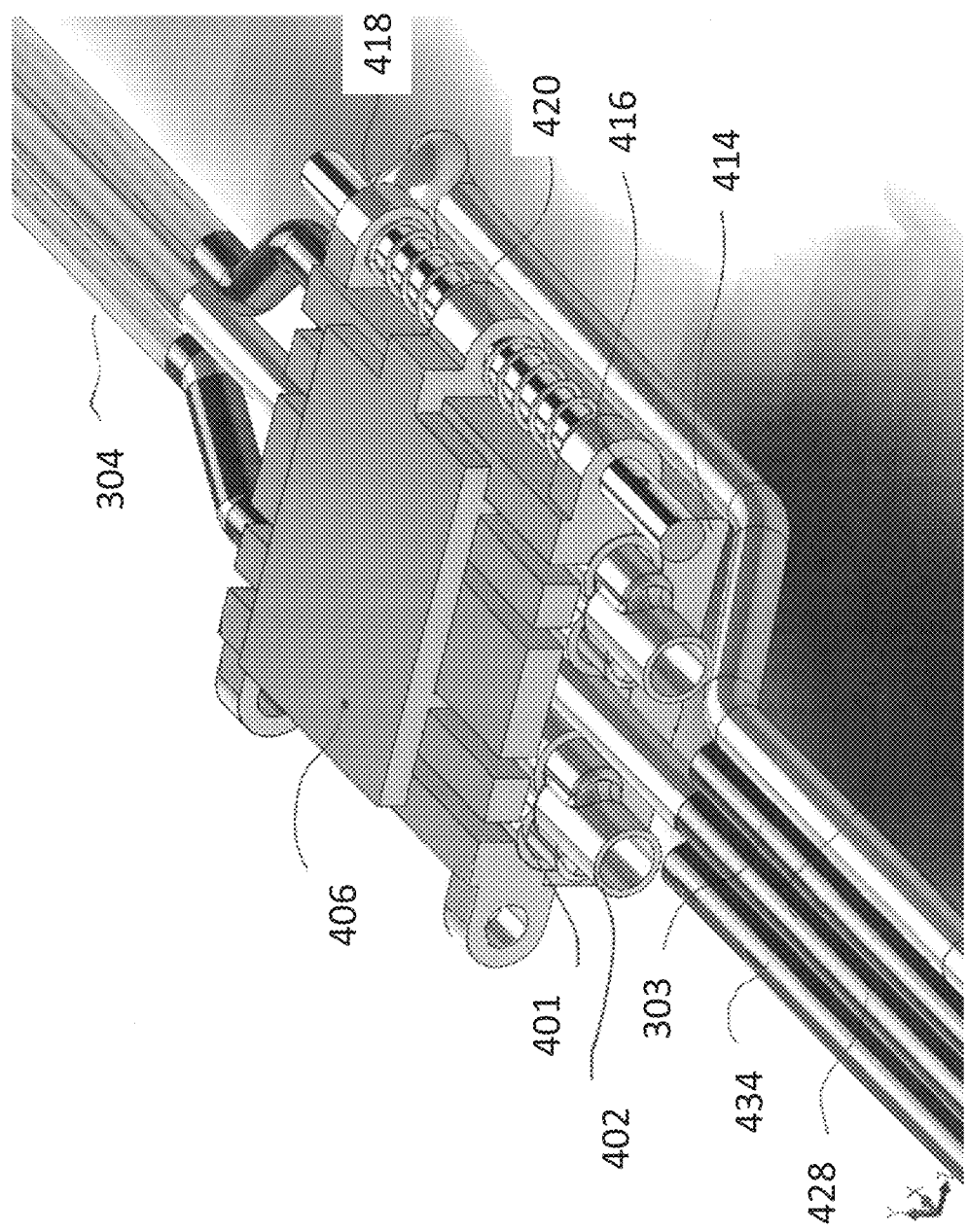
Figure 31:
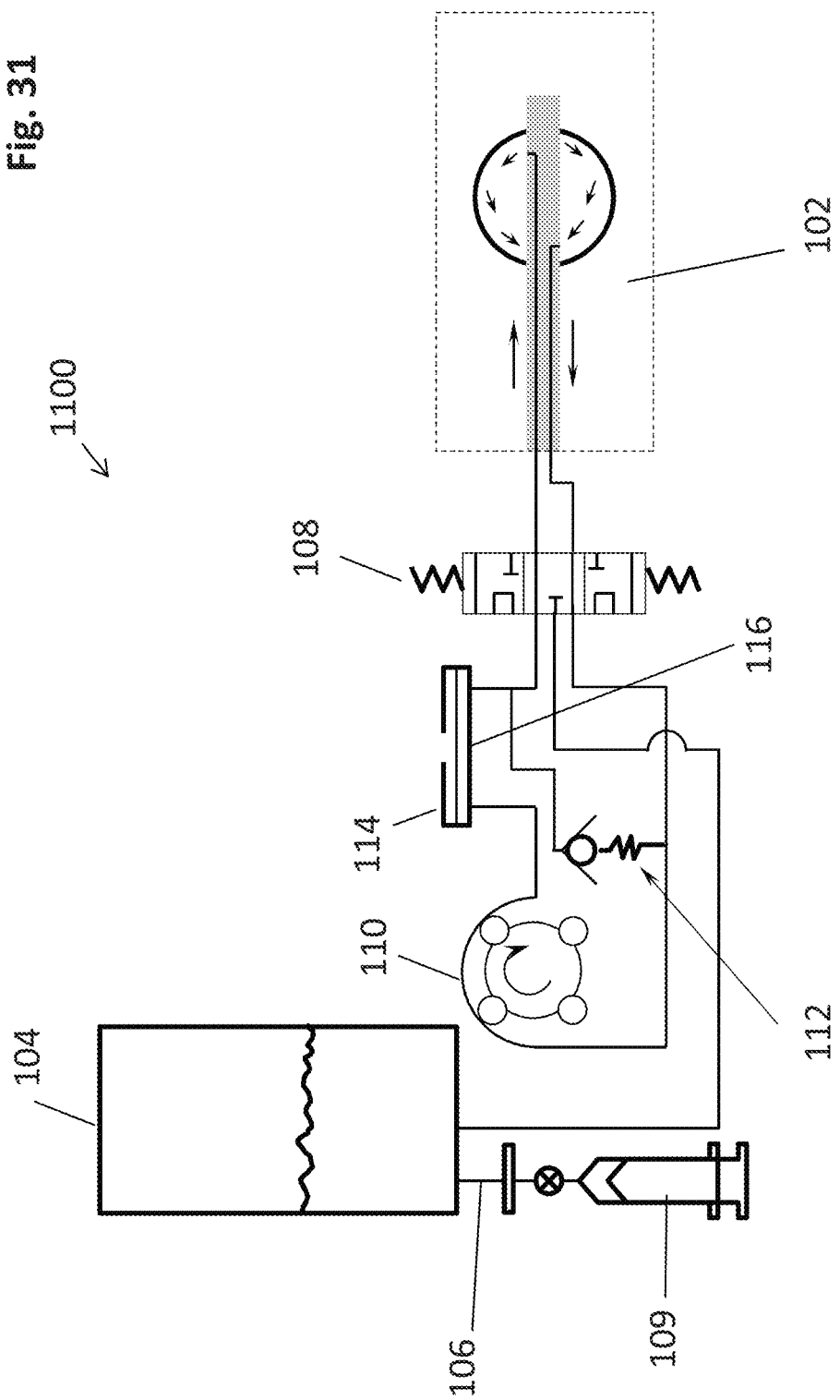
Figure 32:
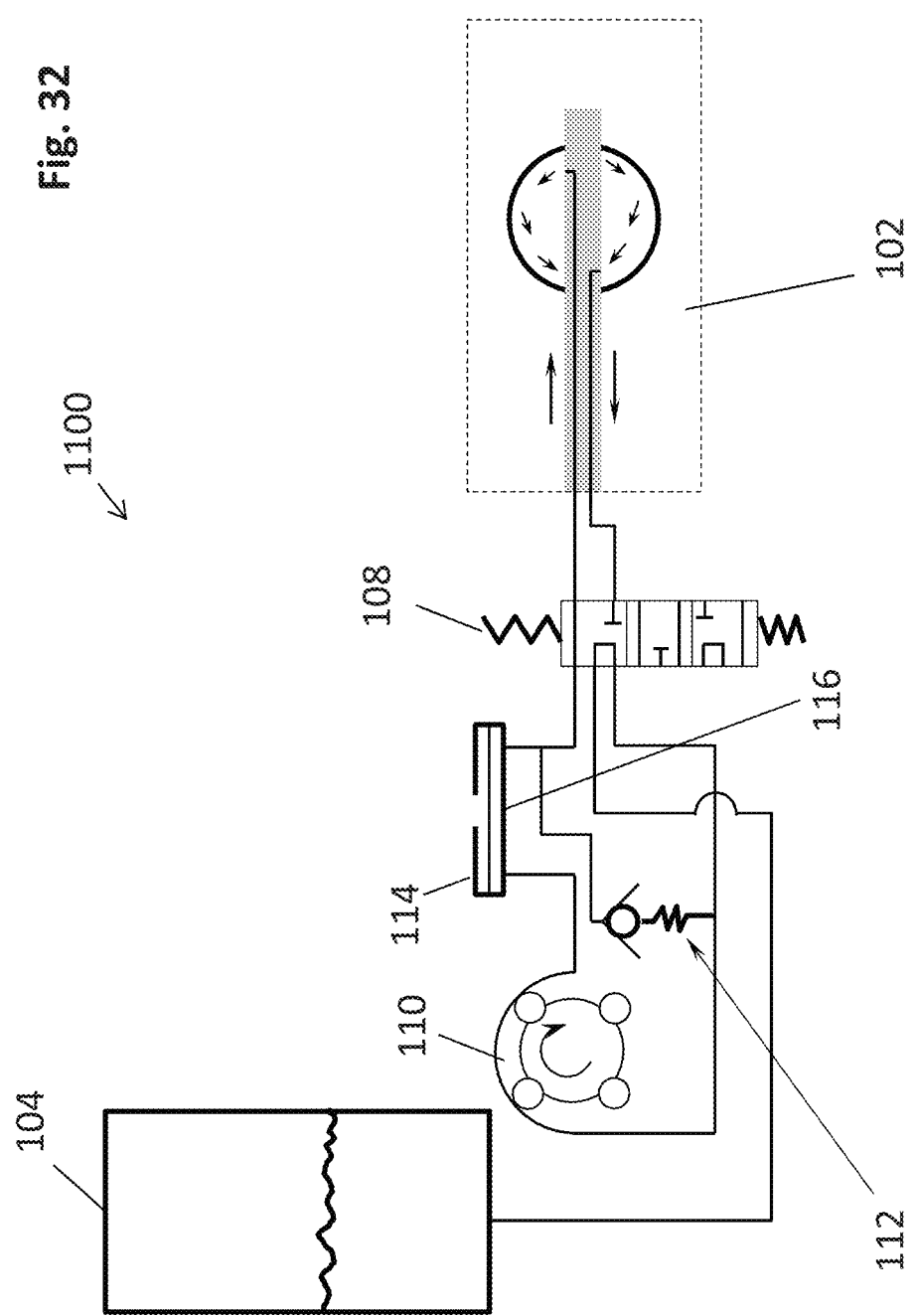
Figure 33:
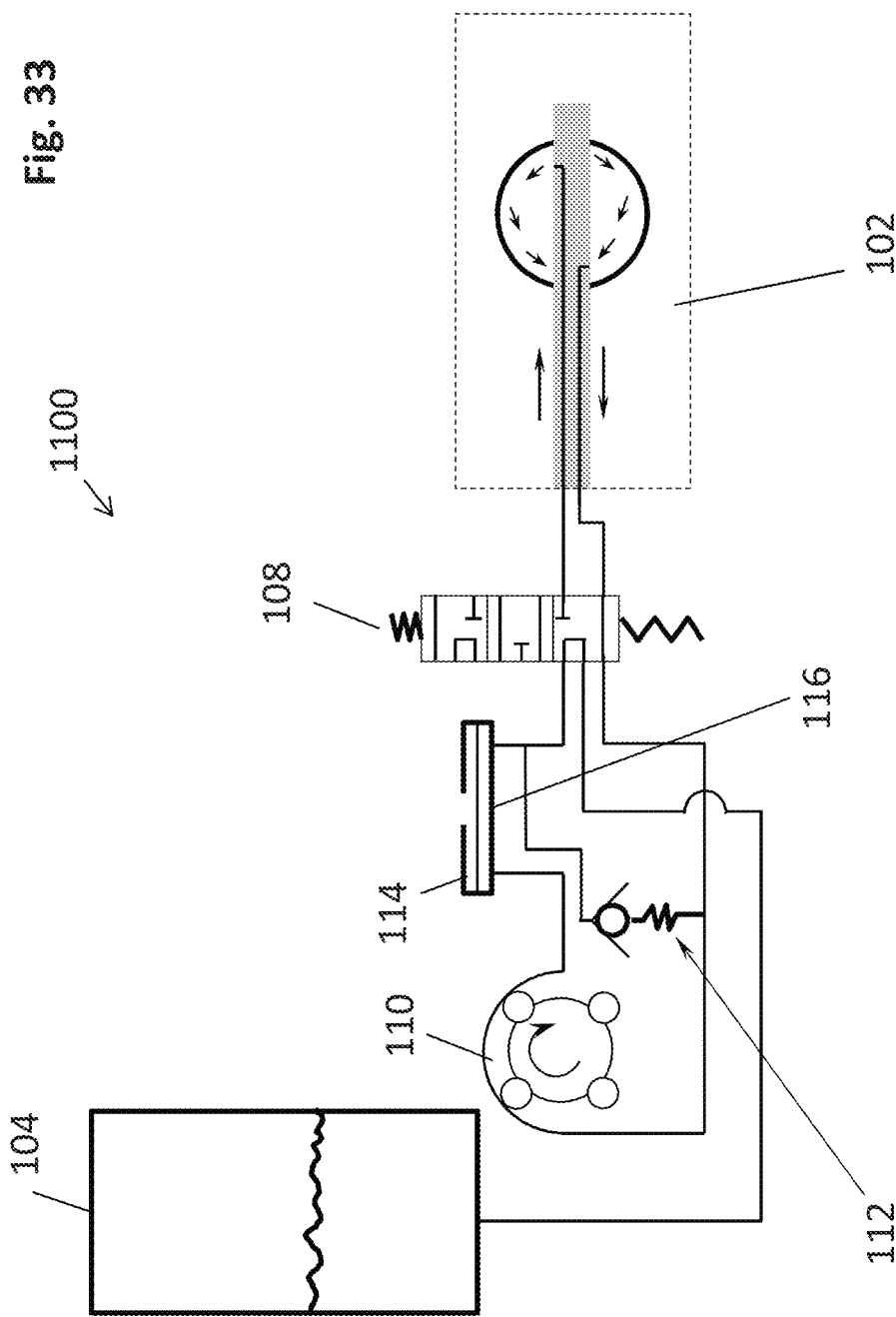
Figure 34:
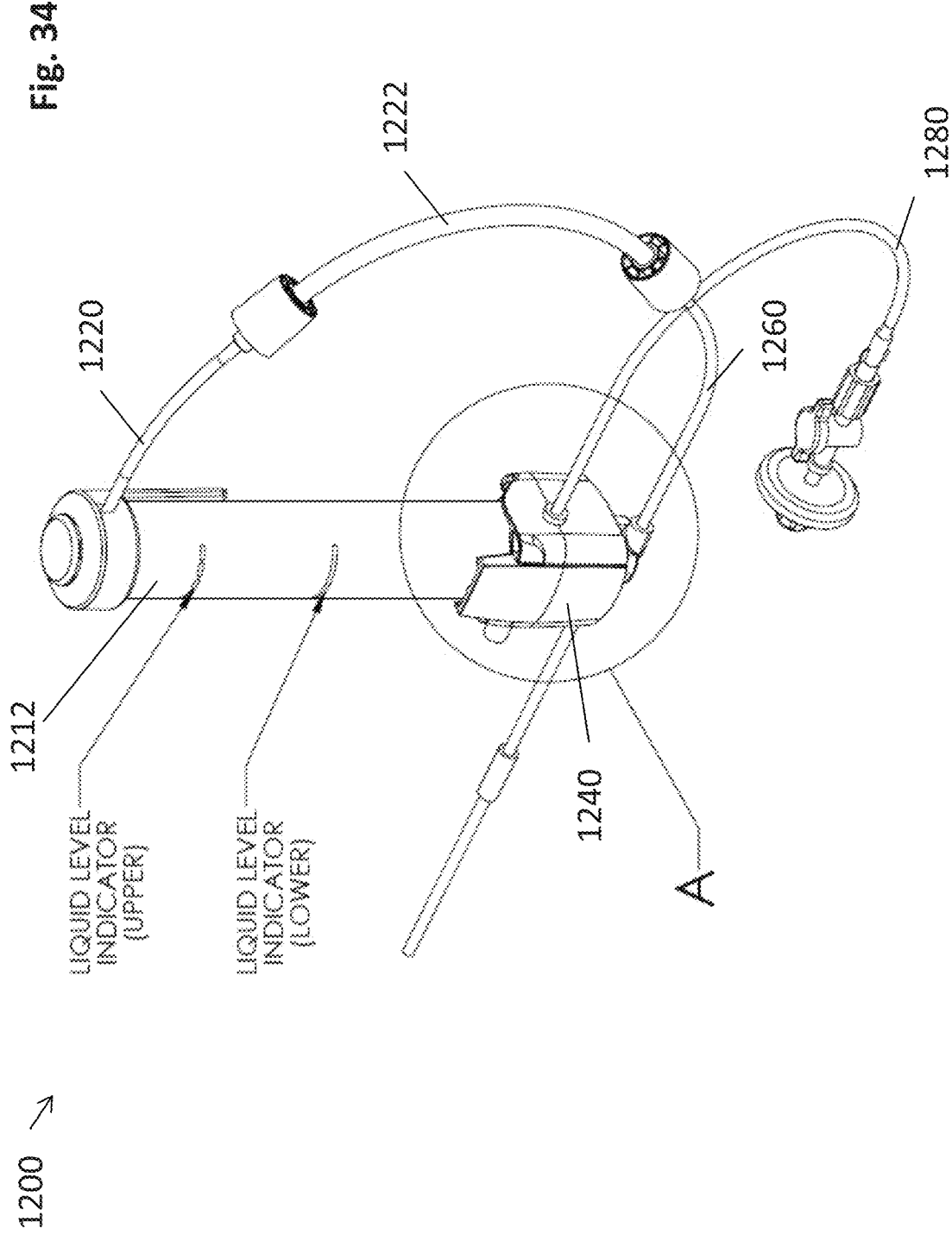
Figure 35:
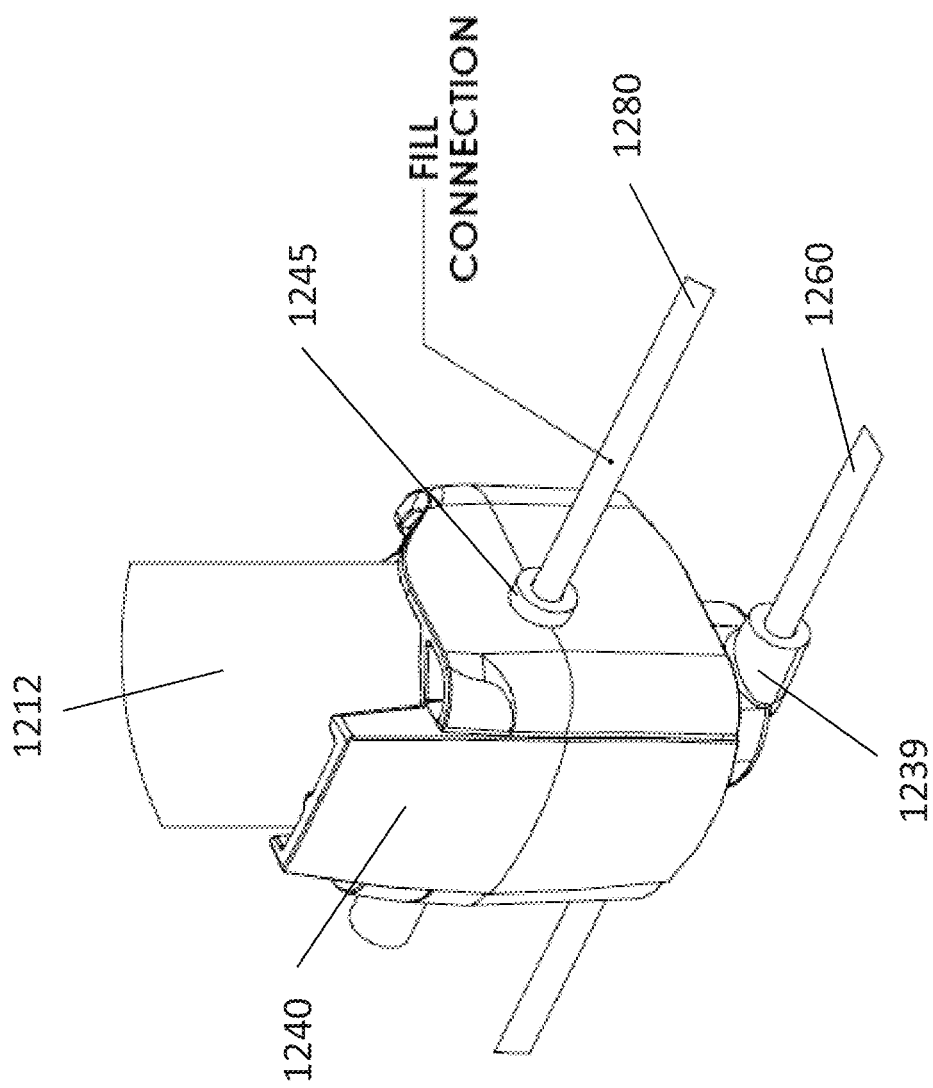
Figure 36:
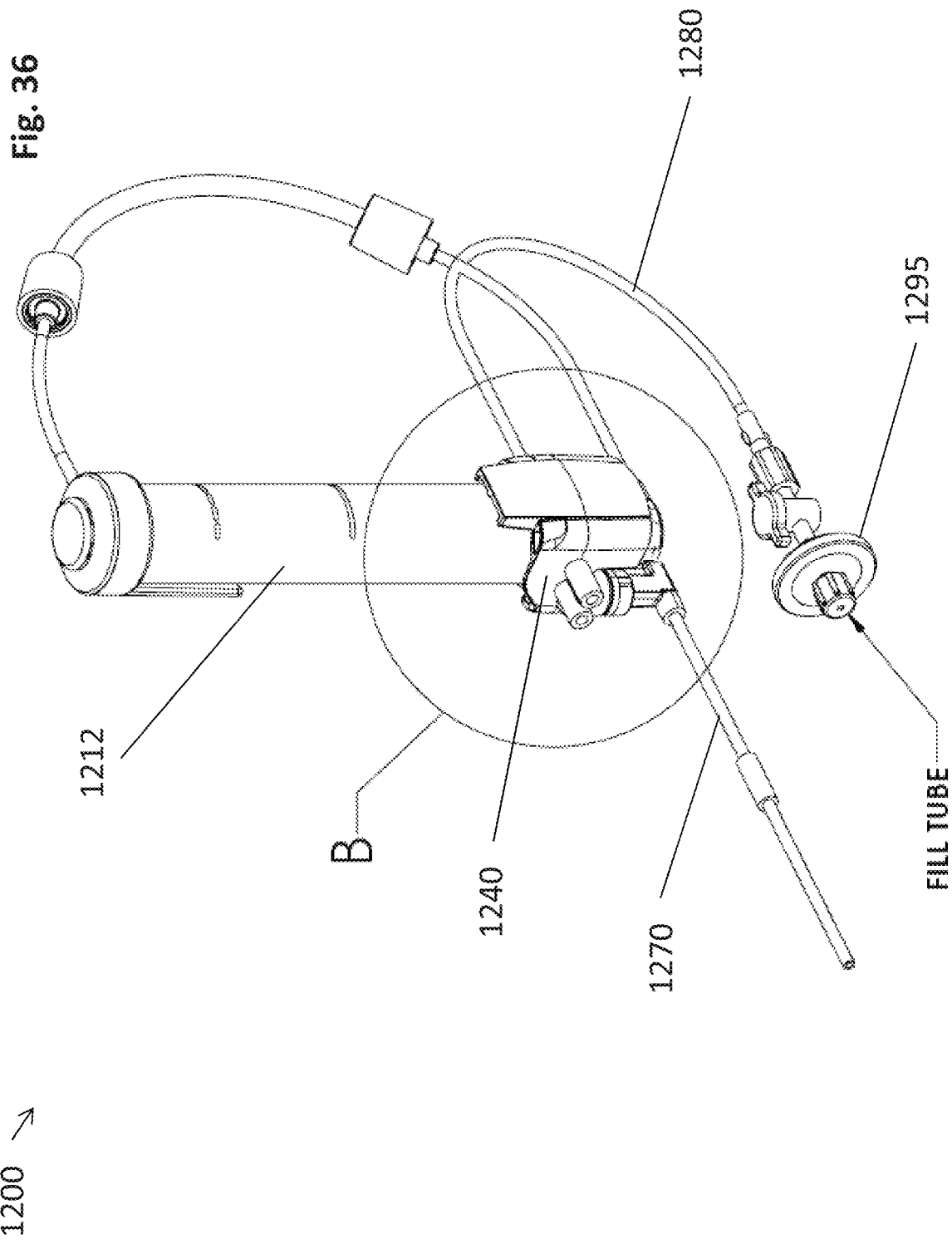
Figure 37:
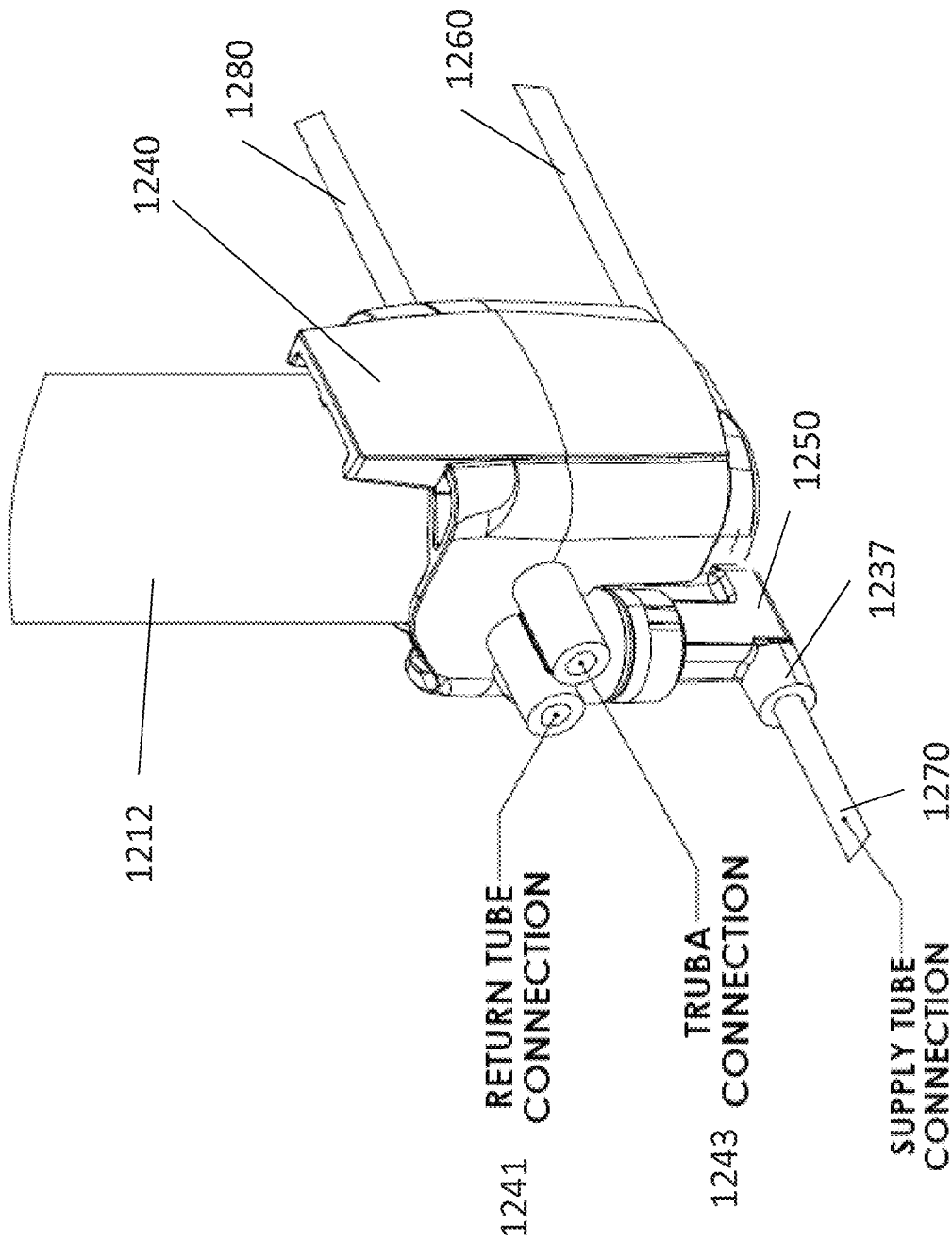
Figure 38:
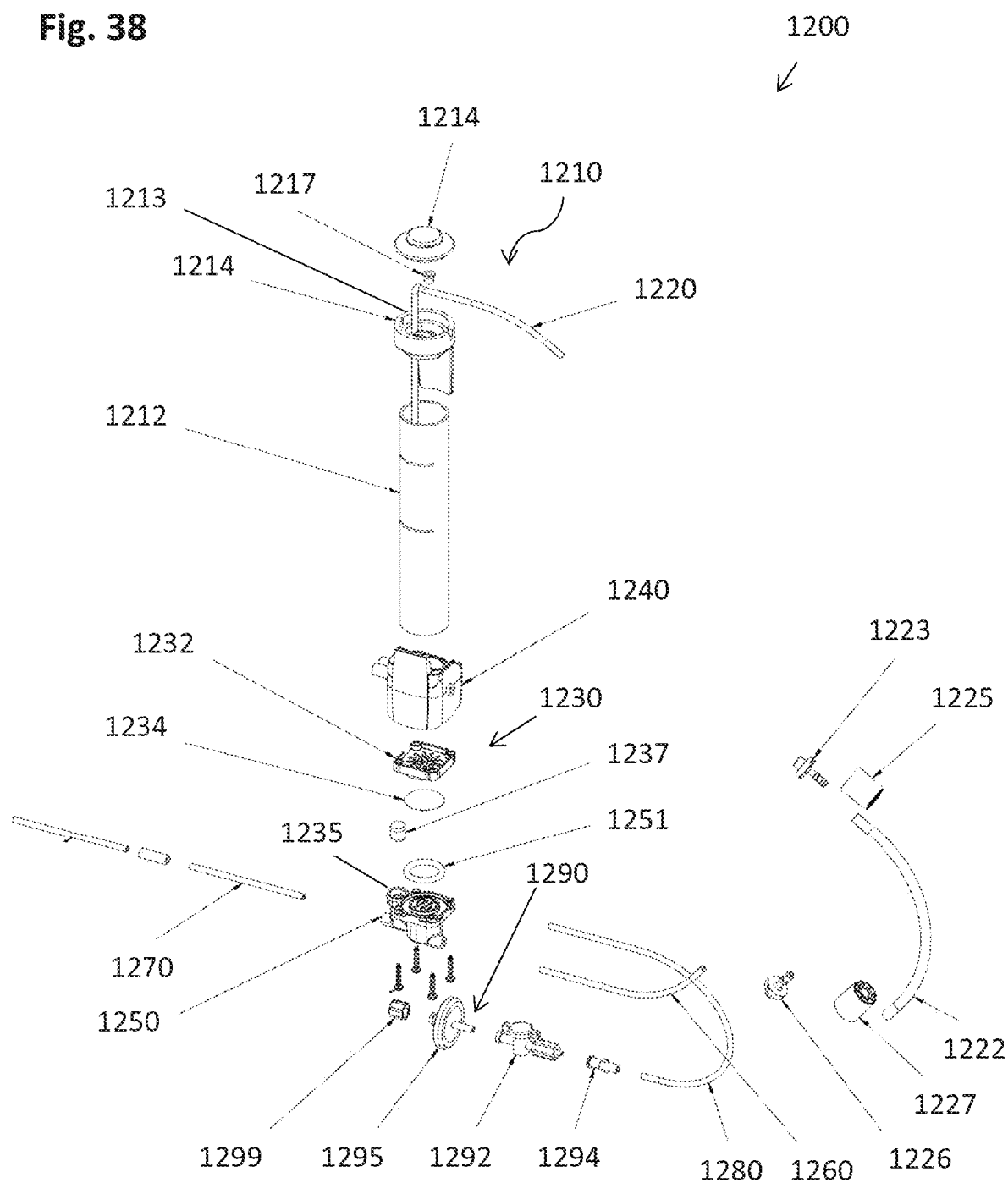

FIG. 24 displays a schematic of a balloon cooling system featuring a peristaltic pump in accordance with one or more embodiments;

FIG. 25 shows a flow diagram of the catheter of the balloon cooling system operating in normal mode in accordance with one or more embodiments;

FIG. 26 shows various operating modes of the valves of the balloon cooling system in accordance with one or more embodiments;

FIG. 27 shows an exemplary configuration of a mode switch valve in an open position in accordance with one or more embodiments;

FIG. 28 shows an exemplary configuration of a mode switch valve in a closed position in accordance with one or more embodiments;

FIG. 29 shows a cross section of an exemplary mode switch valve with four tubes in accordance with one or more embodiments;

FIG. 30 shows a side perspective view of an embodiment of the mode switch valve in accordance with one or more embodiments;

FIG. 31 displays a schematic of an alternative implementation of the balloon fill media control system in a trapped volume state in accordance with one or more embodiments;

FIG. 32 displays a schematic of the alternative implementation of the balloon fill media control system in an inflate state in accordance with one or more embodiments;

FIG. 33 displays a schematic of the alternative implementation of the balloon fill media control system in an deflate state in accordance with one or more embodiments;

FIG. 34 is a right side perspective view of a burette manifold in accordance with one or more embodiments;

FIG. 35 is a right side perspective view of a portion of the burette manifold in accordance with one or more embodiments;

FIG. 36 is a left side perspective view of the burette manifold in accordance with one or more embodiments;

FIG. 37 is a left side perspective view of a portion of the burette manifold in accordance with one or more embodiments; and FIG. 38 is an exploded perspective view of the burette manifold in accordance with one or more embodiments;

DETAILED DESCRIPTION OF CERTAIN EMBODIMENTS ON THE INVENTION

The present disclosure details fluid control systems for filling a balloon catheter with fill media. The fluid control systems of the present disclosure are configured to inflate the balloon catheter to a desired pressure (e.g., approximately 0.2 to 1.0 PSI), maintain the balloon at the desired pressure for a desired duration during the medical procedure (e.g., ablation of heart tissue to treat atrial fibrillation), and deflate the balloon catheter to a desired pressure (or deflate the balloon catheter completely for removal of the catheter from the body). The present fluid control systems allow the balloon catheter to inflate and maintain the balloon catheter at a lower pressure, while keeping the balloon and catheter components cool such that the tissue of the patient is not damaged. Further, the present systems allow a single operator to control the inflation and deflation of the balloon catheter as well as the manipulation of the balloon catheter in the body of the patient during the medical procedure.

Figure 1:
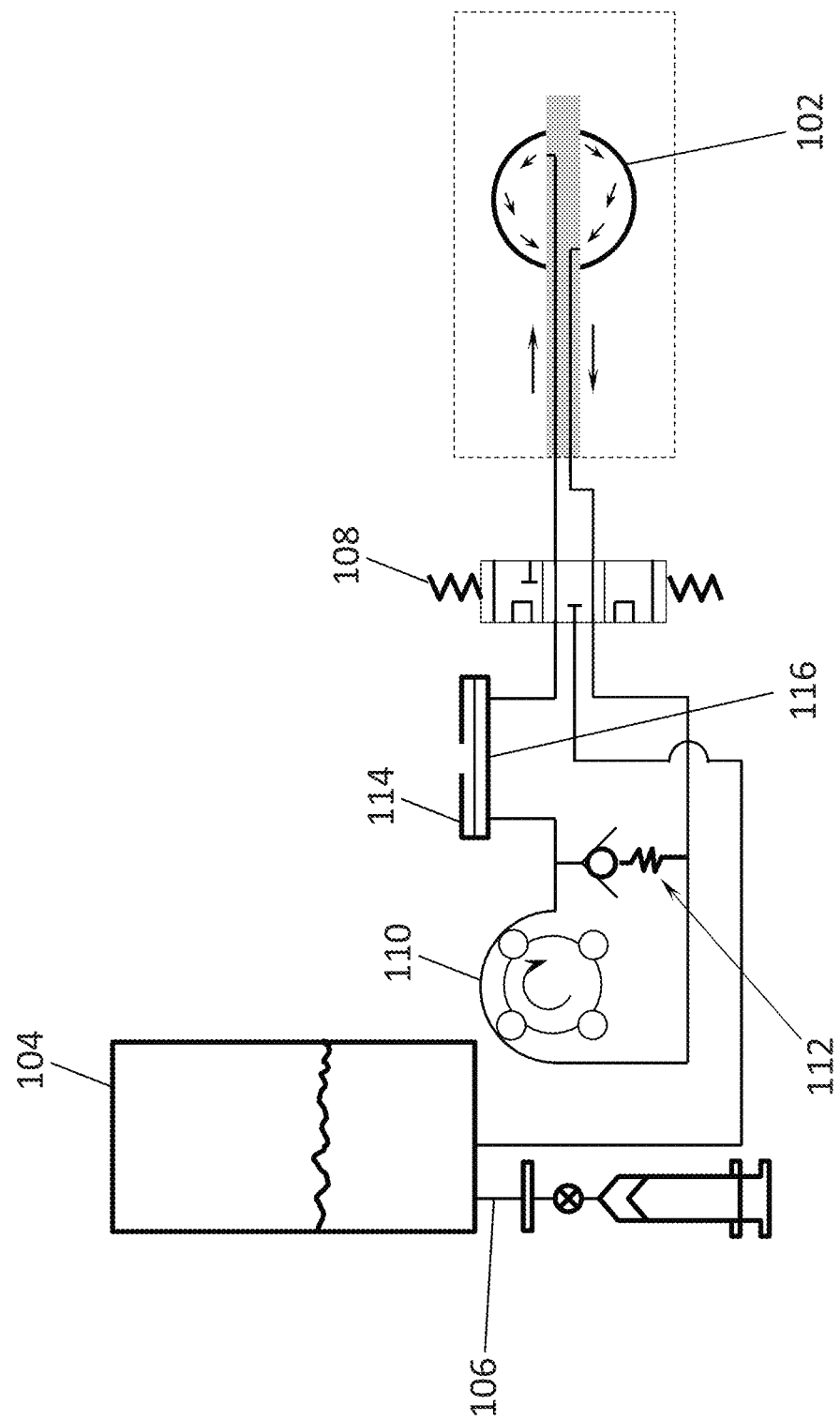
Figure 2:
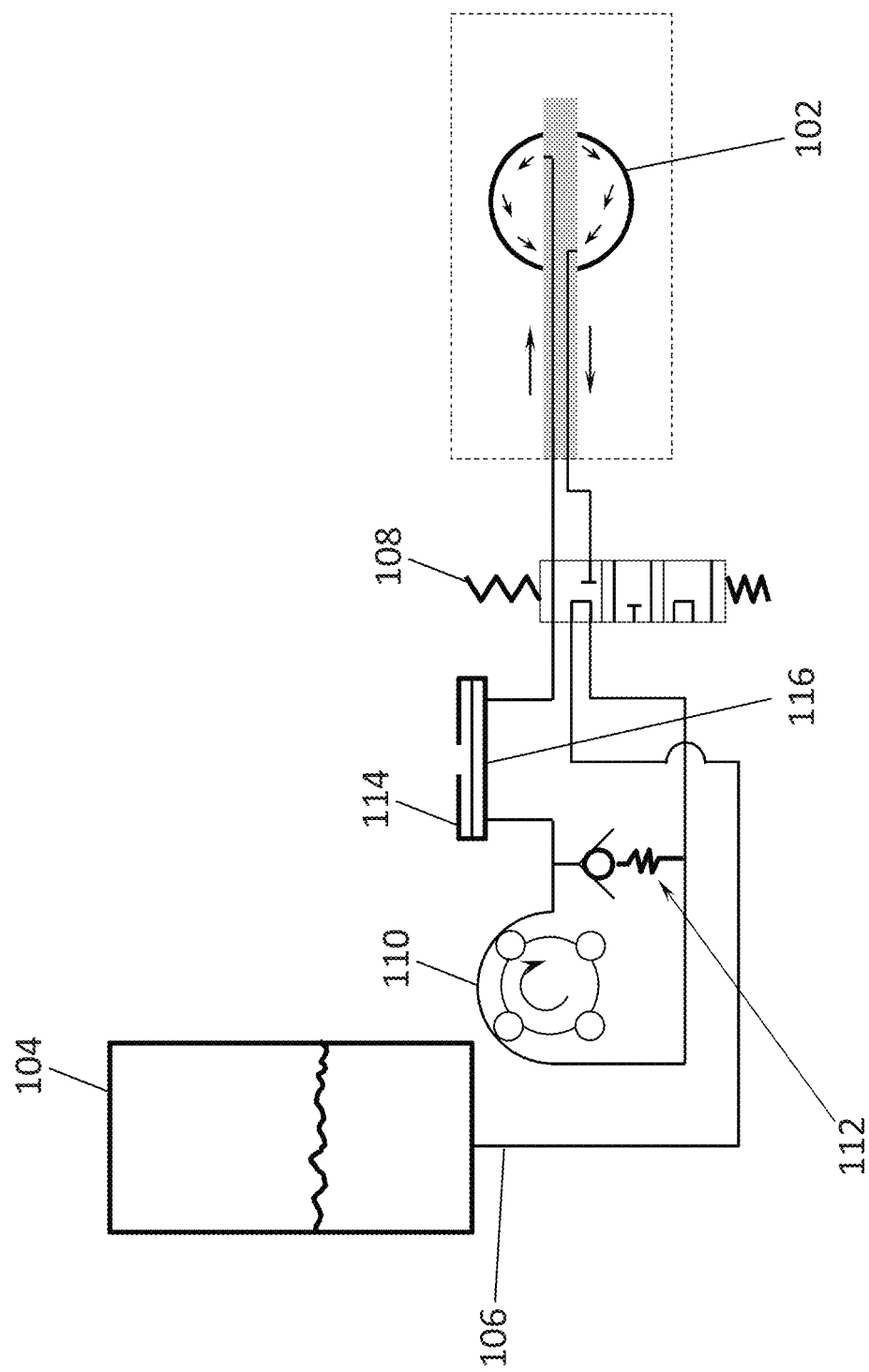
Figure 3:
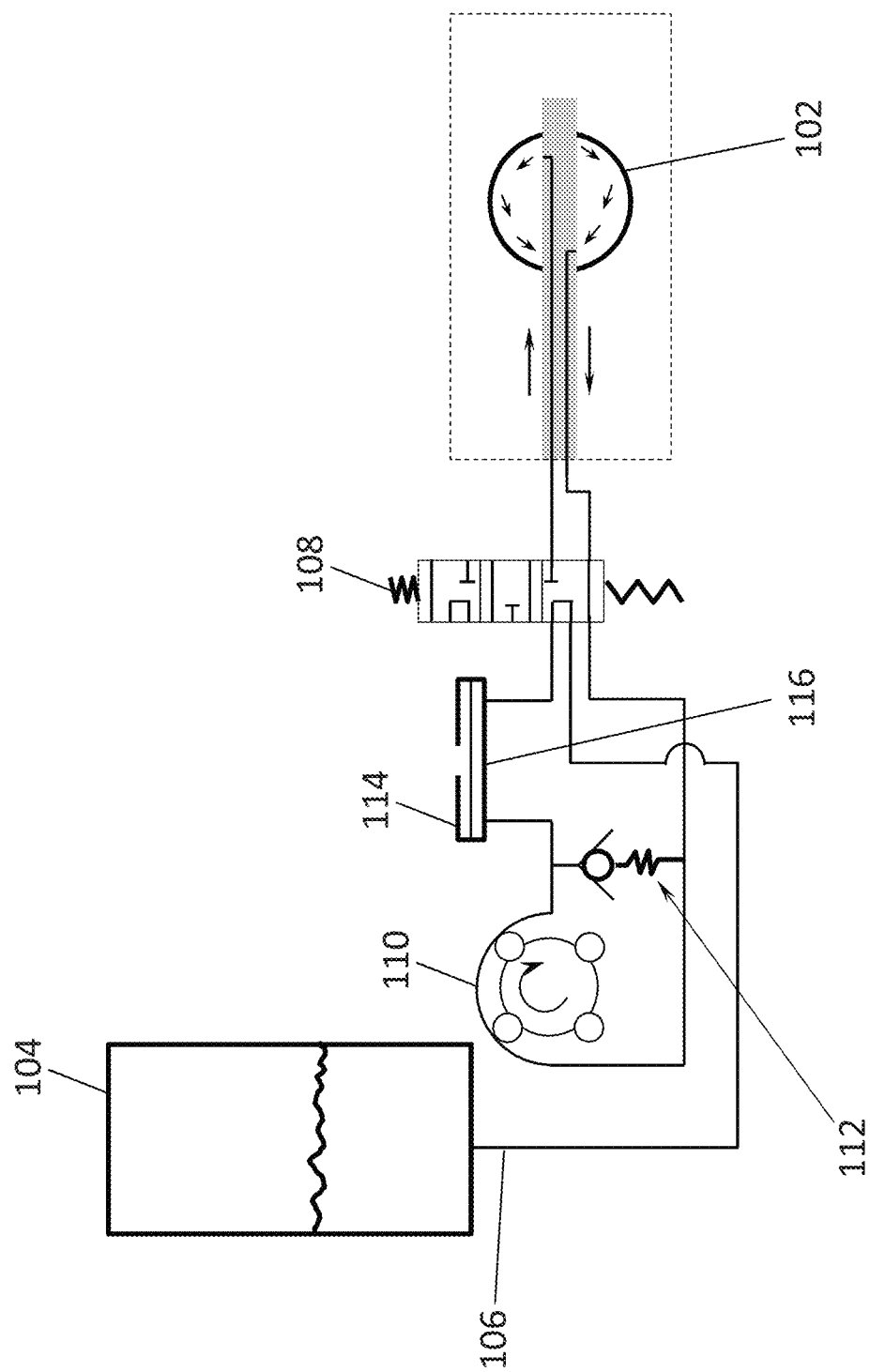

FIGS. 1-3 displays a schematic of a balloon fill media control system 100 of the present application in accordance with one or more embodiments. As shown in FIGS. 1-3, the system 100 generally includes a balloon catheter 102 (e.g., balloon ablation catheter), a balloon fill media reservoir (burette) 104 for holding the balloon fill media having a fill port 106, a remote inflate-deflate valve 108, a volumetric pump 110, a vacuum relief valve 112, and an air separator 114. The system can further include an endoscope having illumination fibers (not shown) for viewing the balloon catheter in the body of the patient during the medical procedure. In particular, via a console, the operator of the system 100 can view an image from the endoscope of the balloon catheter in the body to determine whether the balloon catheter has been inflated (or deflated) the prescribed amount, and whether contact has been achieved between the balloon catheter and the target tissue in order to perform the medical procedure.

As described herein, the present invention is directed to a remote valve assembly that allows the operator to control operation of the catheter and in particular, the remote valve assembly permits the operator to control inflation of the balloon from a remote location from the console (e.g., a location at or proximate the catheter handle).

The inflate-deflate valve 108 is a remote valve assembly that has three states—a "trapped volume" state, an "inflate" state, and a "deflate" state—and is placed in one of these three states by the operator of the catheter. In one or more embodiments, the state of the inflate-deflate valve 108 can be changed by the operator using an actuation mechanism (not shown) operatively connected to the valve 108. In certain embodiments, the actuation mechanism can be operated by the hand of the operator. As shown in FIG. 1, when the operator is not touching the valve 108, the valve 108 automatically assumes a "trapped volume" state through the action of return springs as shown or via other such mechanisms. In the "trapped volume" state, balloon fill media (e.g., a liquid with surface tension similar to water) is circulated by the volumetric pump 110 through the balloon catheter 102. Circulating balloon fill media through the balloon catheter 102 keeps the balloon catheter and all parts of the catheter cool during the medical procedure. For example, in embodiments in which the balloon catheter 102 is used for ablation of heart tissue to treat atrial fibrillation, the balloon fill media is circulated through the balloon catheter 102 to keep the balloon catheter and the remain parts of the catheter cool during energy delivery (ablation) through the catheter into tissue.

Further, in the "trapped volume" state shown in FIG. 1, the volume of balloon fill media contained in system is fixed so the balloon will maintain an inflated state with a constant volume in the balloon while still allowing balloon fill media to circulate into and out of the balloon to perform the desired cooling function. In other words, as shown in FIG. 1, the volume of the balloon fill media already contained in the system is "trapped" in a closed loop, circulating between the volumetric pump 110 and the balloon catheter 102 such that the balloon catheter remains inflated and the balloon catheter 102 does not become overheated during operation.

The air separator 114 of the system 100 can include a porous hydrophobic membrane 116 that is supported in a housing and divides the housing into upper and lower chambers. When a mixture of balloon fill media and air bubbles enter the lower chamber of the air separator 114 (such a mixture is likely to be encountered when balloon fill media is initially introduced into an initially dry system) the air bubbles rise to the top of the lower chamber and are forced into the upper chamber through the porous hydrophobic membrane 116 by the pressure in the lower chamber created by the pump 110. Once in the upper chamber of the air separator 114, air exits to the atmosphere through a vent hole in the upper chamber. Balloon fill media cannot pass through the porous hydrophobic membrane 116 because the hydrophobic nature of the membrane requires a pressure well above the operating pressure of the pump 110 to cause balloon fill media to enter the pores of the membrane. With the system 100 configured as shown in FIG. 1 above, air is easily removed from the flow circuit during initial set up of the catheter.

It will be appreciated that the air separator 114 can be disposed at any number of different locations including at a location that is proximate or attached to the media reservoir (burette) 104.

The balloon catheter 102 and balloon fill media control system 100 are supplied to the user dry. The user initially fills the balloon fill media reservoir (burette) 104 through a fill port 106 connected to the reservoir. The fill port can be fitted with a stopcock and a sterilizing filter that serves as an added assurance that balloon fill media remain sterile as it is introduced into the balloon fill media reservoir. In one or more embodiments, transfer of balloon fill media from a storage vial into the reservoir 104 is done with the aid of a syringe as shown in FIG. 1 (the fill port 106 has been excluded from FIGS. 2 and 3 only for ease of illustration).

In one or more embodiments, the volumetric pump 110 is a peristaltic pump also called a roller pump. Such a pump includes a length of disposable elastic tubing that is installed in a durable pump head. In implementations in which the catheter is a balloon ablation catheter, the durable pump head is part of the durable system used to supply the appropriate ablation energy to the catheter as well as perform other functions such as displaying endoscopic images from an endoscope indwelling the ablation catheter, for example. The disposable elastic tubing, such as silicone rubber tubing, can then be part of a disposable balloon catheter and balloon fill media control system.

FIG. 2 displays a schematic of the balloon fill media control system 100 where the inflate-deflate valve 108 is in the "inflate" state or mode. When the user places the inflate-deflate valve 108 in the "inflate" state (e.g., via the actuation mechanism), fluid is drawn out of the balloon fill media reservoir 104 and is pumped into the balloon 102 increasing the balloon size. In this manner, the balloon 102 can be filled to a range of continuously variable sizes in order to best match the anatomy of the tissue of the patient at the operating site. When the user (operator) removes his or her hand from the actuation mechanism of the valve 108, the valve 108 will return to the "trapped volume" state shown in FIG. 1 and the balloon size to which the balloon has been inflated is maintained by the "trapped volume" mode of the system 100.

FIG. 3 displays a schematic of the balloon fill media control system 100 where the inflate-deflate valve 108 is in the "deflate" state or mode. When the user (operator) places the inflate-deflate valve 108 in the "deflate" mode, fluid is drawn out of the balloon 102 and is pumped (using volumetric pump 110) back to the balloon fill media reservoir 104, thereby decreasing the balloon size. In this manner, the balloon 102 can be decreased in size through a continuously variable range of sizes to in order to best match the anatomy of the tissue of the patient. When the user (operator) removes his or her hand from the actuation mechanism of the valve 108, the valve returns to the "trapped volume" state (shown in FIG. 1) and the balloon size to which the balloon 102 has been deflated to is maintained by the trapped volume mode of the system 100. Alternatively, the user can hold the valve 108 in the "deflate" mode shown in FIG. 3 in order to fully deflate the balloon 102. Full deflation of the balloon catheter 102 is generally done at the beginning of the medical procedure in order to introduce the fully deflated balloon into the patient's body, and at the end of the medical procedure to remove the balloon catheter 102 from the patient.

The relief valve 112 shown in FIGS. 1-3 limits the differential pressure that can be generated by the volumetric pump 110. In one or more embodiments, the relief valve 112 is configured such that the pressure limit is between approximately 5 and 20 PSI, and preferably between 7 and 12 PSI. Limiting the differential pressure of the pump 110 serves a number of purposes. First, limiting the pressure developed by the pump 110 prevents excessive pressure from being developed in the balloon 102 should the user (operator) mistakenly maintain the inflate-deflate valve 108 in the "inflate" mode continuously. Another benefit of limiting the pump differential pressure is that doing so prevents the pressure in the lower chamber of the air separator 114 from exceeding the pressure at which balloon fill media may be forced through the hydrophobic membrane 116. Another reason for limiting the differential pressure that the pump 110 can generate is that this will limit the level of vacuum created by the pump 110 when the balloon 102 has been totally deflated. Limiting the amount of vacuum is important because too much vacuum applied to the balloon fill media can pull gas dissolved in the balloon fill media out of solution resulting in gas bubbles that can enter the balloon catheter 102.

Rocker Switch Embodiment

FIGS. 4-8 display a balloon fill media control system 200 that similarly comprises a valve assembly that has a "trapped volume" state, an "inflate" state, and a "deflate" state. Like the system 100 as exemplified in FIGS. 1-3, the valve assembly of system 200 can be placed in one of these three states by the operator. As such, the circulation of the balloon fill media in system 200 during the three "states" is substantially the same as the circulation of balloon fill media described in reference to the embodiment of FIGS. 1-3, except with regards to how the fill media passes through the valve assembly, as discussed in further detail below.

It will therefore be appreciated that the valve assembly of FIGS. 4-8 can be a substitute for valve 108 and thus placed at the location of valve 108 in FIG. 1.

Figure 4:
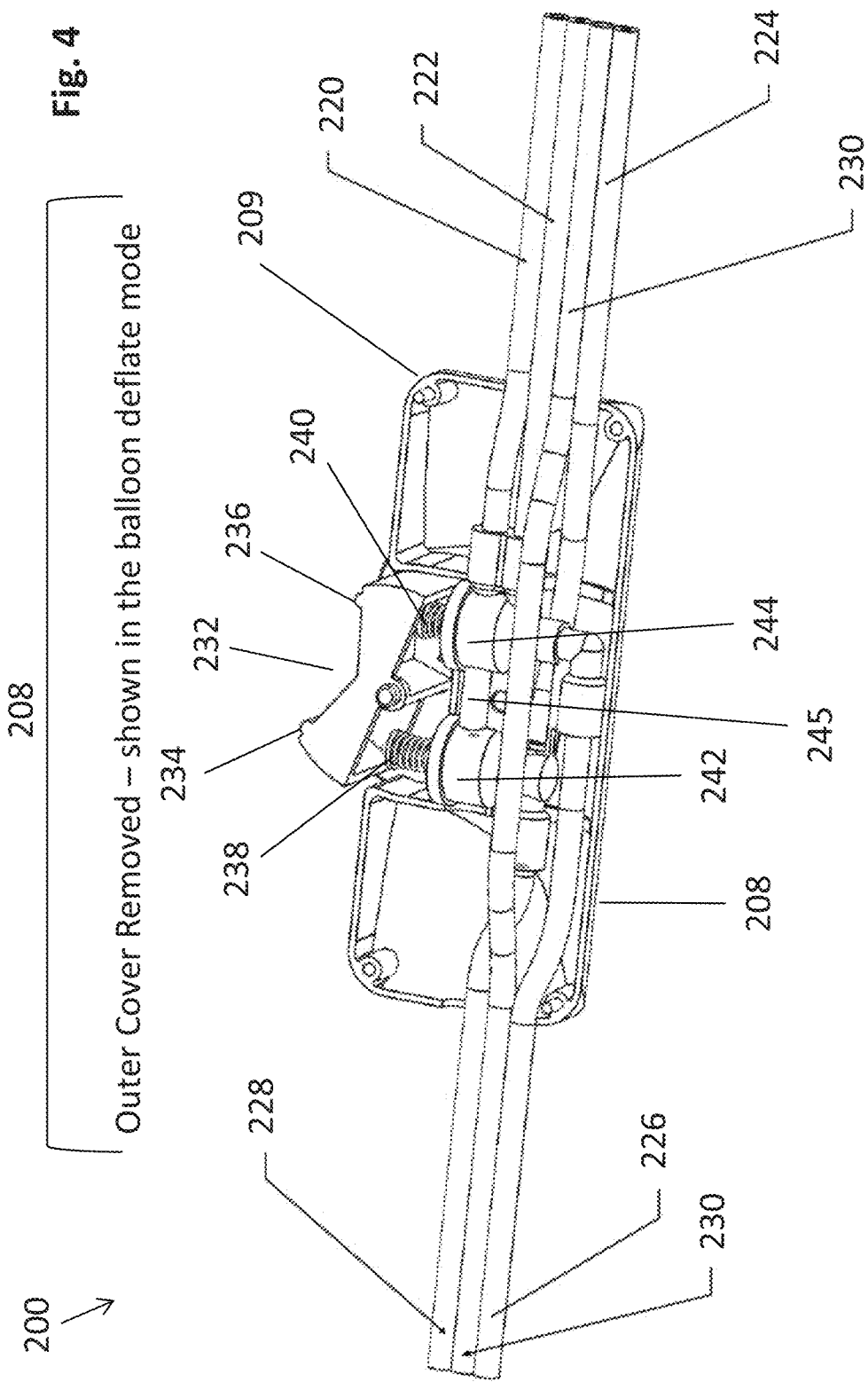

FIG. 4 displays a side perspective view of the balloon fill media control system 200 showing the inside of the rocker valve assembly 208 (i.e., the rocker valve assembly 208 with a portion of the outer cover (housing) 209 removed). Like the system 100 of FIGS. 1-3, the system 200 can include a balloon catheter, a balloon fill media reservoir having a fill port, a volumetric pump, a vacuum relief valve and an air separator substantially as shown in system 100 (not shown in FIGS. 4-8). The system 200 also comprises a rocker valve assembly 208 having a housing 209. As mentioned above, the rocker valve assembly 208 has a "trapped volume" state, an "inflate" state, and a "deflate" state. The system 200 also comprises a number of conduits or tubes, including a central burette tube 220, a pump feed 222, a pump return 224, a catheter feed 226, and a catheter return 228. The tubes are configured to circulate fluid (e.g., balloon fill media) through the system 200. The system 200 can further comprise at least one illumination fiber 230 that can be used in conjunction with an endoscope to determine whether contact has been achieved between the balloon catheter and the target tissue in the body of the patient.

As further shown in FIG. 4, the rocker valve assembly 208 features a rocker switch 232 having a first end 234 and a second end 236, where the rocker switch 232 is the actuation mechanism for selectively moving the valve assembly 208 between a "trapped volume" state, an "inflate" state, and a "deflate" state. For example, when the operator presses on the first end 234, the valve assembly 208 is in the "inflate" state, and when the operator presses on the second end 236, the valve assembly 208 is in the "deflate" state (as shown in FIG. 4). When the operator is not pressing on either the first or second end of the rocker switch 232, the switch 232 automatically returns to the "trapped volume" state. In other words, when the rocker switch 232 is not being manipulated by the user (operator), it defaults to the "trapped volume" state. The rocker valve assembly 208 also features a first spring 238 and a second spring 240, the springs 238 and 240 being operatively connected to respective plungers that are configured to move within into a first channel (or first reservoir space) 242 and a second channel (or second reservoir space) 244, respectively. FIG. 4 further shows the outer walls of each of the channels 242, 244.

It will be appreciated and is described in more detail below that the rocker valve assembly 208 can be thought of has having two distinct valve assemblies that are generally defined by channels 242, 244 as shown in FIG. 4. Fluid communication between the two valve assemblies is provided by a cross channel 245 that permits fluid within one valve assembly to flow across to the other valve assembly.

Figure 5:
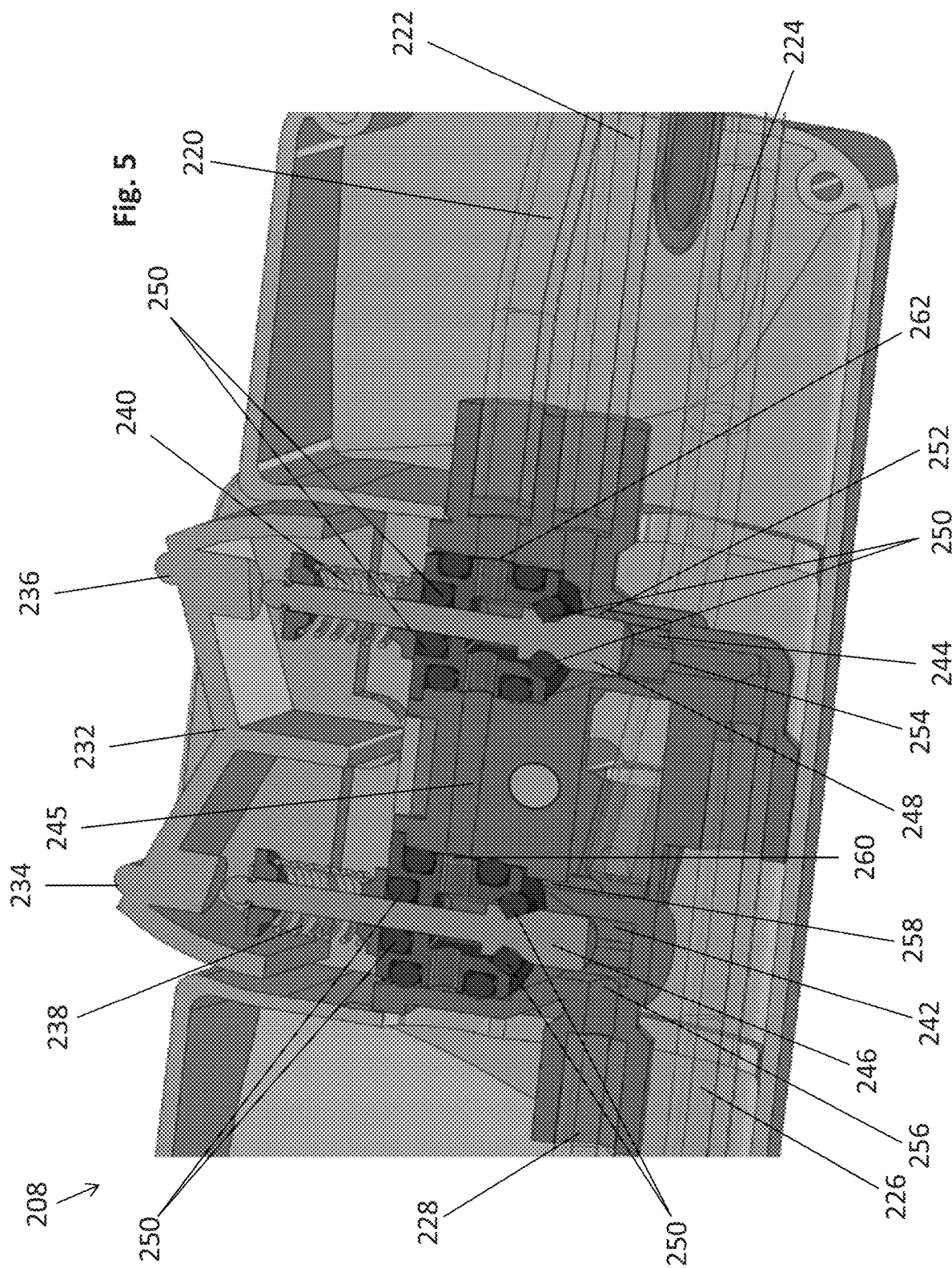

FIG. 5 displays a cross section of the rocker valve assembly 208, showing the inner portions of the valve assembly 208 in accordance with one or more embodiments.

In FIG. 5, the rocker valve assembly 208 is shown without the outer wall of the first and second channels 242 and 244 such that the remaining inner portions are visible. As shown in FIG. 5, the rocker valve assembly 208 can further comprise a first plunger 246 and a second plunger 248, where the first plunger 246 is operatively connected to and acted upon by the first spring 238 and the second plunger 248 is operatively connected to and acted upon by the second spring 240. As a result of user manipulation of the rocker switch 232, the first plunger 246 is configured to selectively move within the first channel 242 and the second plunger 248 configured to selective move within the second channel 244. For example, when the rocker valve assembly is in the "trapped volume" mode as shown in FIG. 5, the distal end of each plunger (246, 248) remains approximately in the middle of their respective channels (242, 244).

When the first end 234 of the switch 232 is depressed by the user (i.e., "inflate" mode), the first end 234 exerts a downward force on the proximal end of the first plunger 246, causing a distal portion of the plunger 246 to move to the bottom of the first channel 242. This is due to an underside of rocker switch 232 having a protrusion at end 234 and at end 236. When the respective end 234, 236 is pressed down, the respective protrusion contacts and drives the respective plunger down. The underside protrusion at the end 234, 236 that is not pressed down does not contact the plunger (it is elevated thereto) and thus, the plunger remains in its normal rest position.

In contrast, when the second end 236 of the rocker switch 232 is depressed by the user (i.e., "deflate" mode), the inverse action occurs. More specifically, the second end 236 exerts a downward force on the proximal end of the second plunger 248, causing a distal portion of the second plunger 248 to move to the bottom of the second channel 244.

When the user (operator) releases the rocker switch 232 (i.e., stops pressing either the first end 234 or second end 236), the springs 238, 240 allow the rocker switch to revert back to the "trapped volume" mode, which is its equilibrium position. In other words, when there is no additional downward force applied to either end of the switch 232, the valve assembly 208 reverts back to its equilibrium position in which both plungers 246, 248 remains approximately in the middle of their respective channels 242, 244 due to the biasing force pulling plungers upward to the rest positions.

With continued reference to FIG. 5, the rocker valve assembly 208 can also include o-rings 250, where the plungers 246, 248 each abut two pairs of o-rings 250. For each plunger, one of the pair of o-rings 250 abuts the distal portion of the plunger to help seal the channels (242, 244) from liquid (e.g., balloon fill media) when the plunger is in its most downward position. As such, these o-rings 250 prevent fluid from one tube or channel from unintentionally commingling with the fluid from another tube or channel, as discussed in further detail below. Likewise, for each plunger, the pair of o-rings 250 abutting the proximal portion of the plunger (i.e., nearest to the springs) prevents fluid from leaking out of the channels to the area of the valve assembly 208 that includes the switch 232. In certain embodiments, such as the embodiment of FIG. 5, one or more additional o-rings can be included in the area surrounding each plunger. These additional o-rings can further help to seal the channels and tubes of the valve assembly 208 and prevent leakage of fluid to the outside of the valve assembly 208.

Trapped Volume Mode

As mentioned above, the circulation of the balloon fill media in system 200 during the three "states" is substantially the same as the circulation of balloon fill media described in reference to the embodiment of FIGS. 1-3 (system 100), except with regards to how the fill media passes through the rocker valve assembly 208. For instance, when the rocker valve assembly 208 is in the "trapped volume" state, the volume of the balloon fill media already contained in the system is "trapped" in a closed loop, circulating between the volumetric pump and the balloon catheter such that the balloon catheter remains inflated and the balloon catheter 102 does not become overheated during operation. With reference to FIG. 5, in order to accomplish the closed loop circulation of the fill media in the "trapped volume" mode using the rocker valve assembly, fluid in the pump feed 222 is transferred to the catheter feed 226 for transport to the catheter, and fluid returning from the catheter is transfer from the catheter return 228 to the pump return 224 for transport back to the pump.

The fill media from the pump transfers from the pump feed 222 to the catheter feed 226 via a conduit 252 and the second channel 244. More specifically, as shown in FIG. 5, when the second plunger 248 is in its "trapped volume" position, conduit 252 is in fluid communication with pump feed 222 and the second channel 244. Accordingly, fluid (e.g., fill media) in the pump feed 222 flows into conduit 252 and then flows into the bottom of the second channel 244, which is fluidly connected to catheter feed 226 via an aperture 254. As such, at the bottom of second channel 244, the fluid flows from the second channel 244 through the aperture 254 and into the catheter feed 226 for transport to the balloon catheter.

Similarly, the fill media returning from the balloon catheter transfers from the catheter return 228 to the pump return 224 via apertures 256 and 258. More specifically, as shown in FIG. 5, when the first plunger 246 is in its "trapped volume" position, the aperture 256 is in fluid communication with the catheter return 228 and the first channel 242. As such, fluid returning from the catheter in catheter return 228 empties into the bottom portion of first channel 242 via aperture 256. Once there is enough fluid to fill the bottom portion of first channel 242, the fluid reaches the height of aperture 258 and begins to enter aperture 258, which empties into pump return 224. Accordingly, as the fluid enters aperture 258, the fluid then flows into pump return 224 for transport to the pump. The flow of the liquid (e.g., fill media) during the "trapped volume" state for system 200 is shown in FIG. 6.

Figure 6:
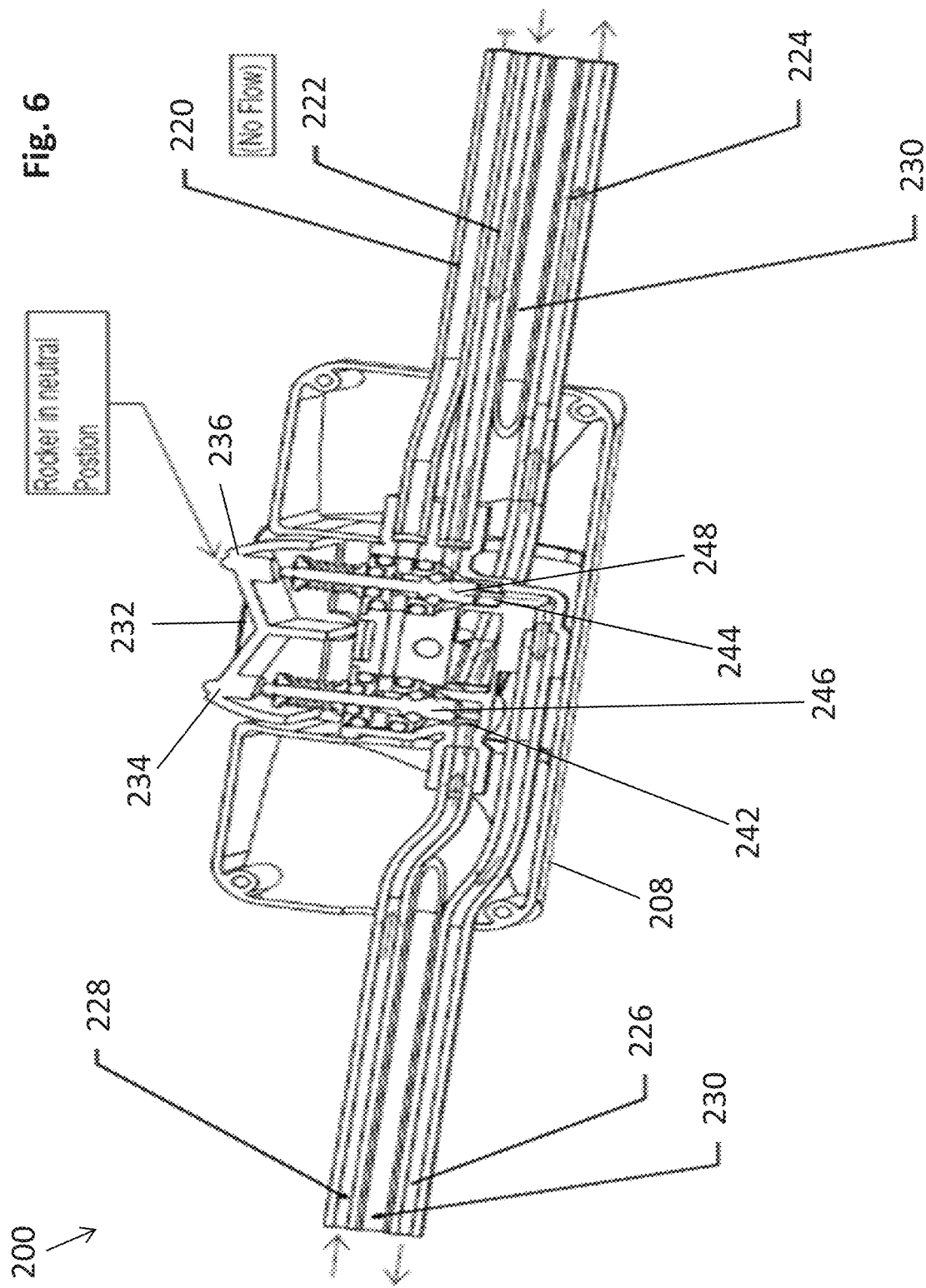

As shown in FIG. 6 and as discussed above, in the "trapped volume" mode, the fluid in the pump feed 222 transfers to the catheter feed 226 for transport to the catheter, and fluid returning from the catheter transfers from the catheter return 228 to the pump return 224 for transport back to the pump. In the "trapped volume" mode, there is also no fluid flow in the central burette tube 220 as no additional fluid is being transferred from the balloon fill media reservoir to the rest of the system. In addition, it will be appreciated that any fluid in the central burette tube 220 is fluidly isolated from the other chambers and conduits by positions of the plungers and the o-rings associated therewith.

Inflate Mode

Figure 7:
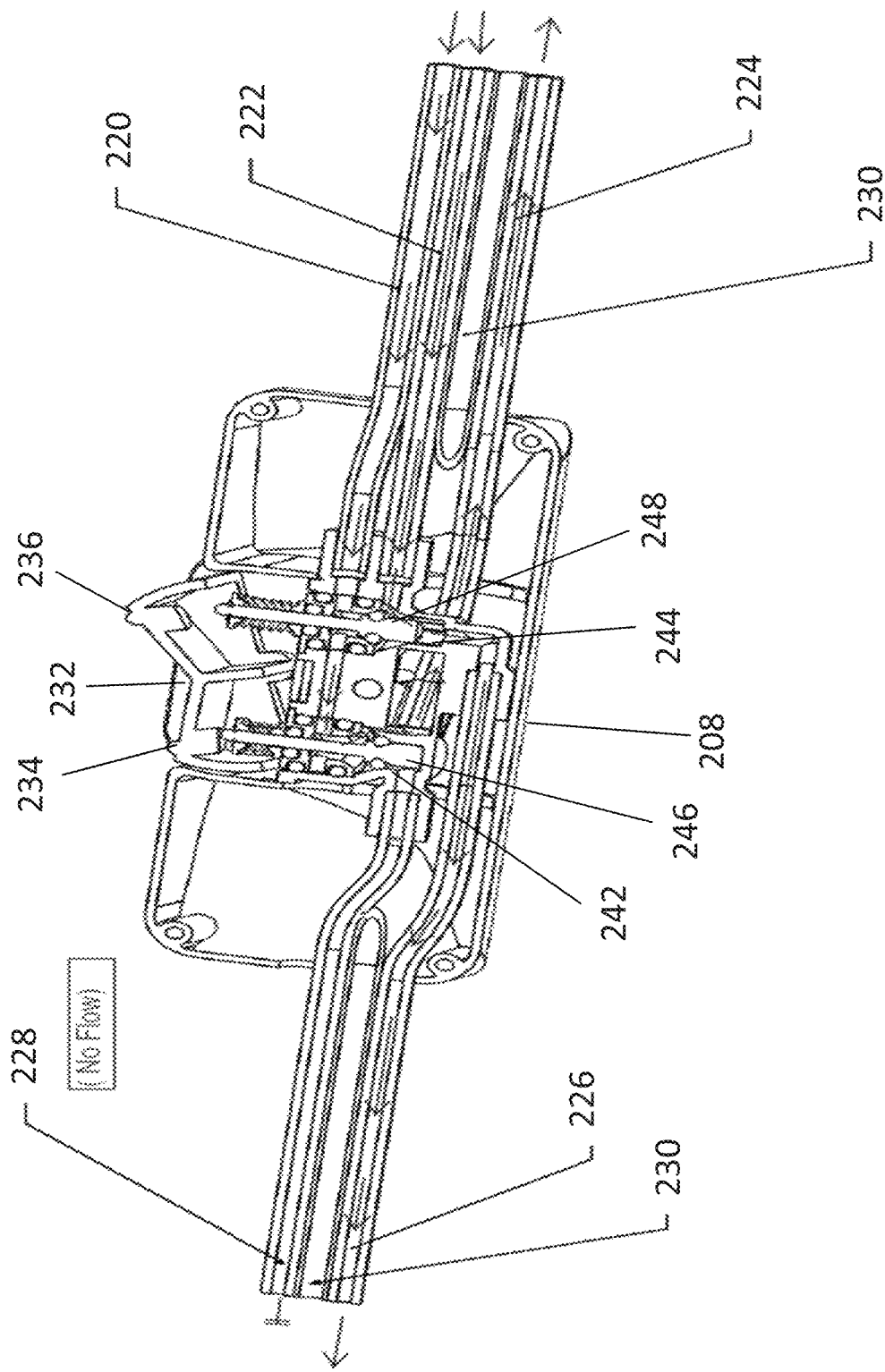

The flow of the liquid (e.g., fill media) during the "inflate" state for valve assembly 208 is shown in FIG. 7. With reference to FIGS. 5 and 7, in the "inflate" state, the first end 234 of the rocker switch 232 is depressed by the user (i.e., "inflate" mode) and exerts a downward force on the proximal end of the first plunger 246, causing a distal portion of the plunger 246 to move to the bottom of the first channel 242. As such, the distal portion of the plunger 246 blocks the first channel 242, thereby preventing substantially any fluid in the catheter return 228 from passing through to channel 242. Because the second plunger 248 is in substantially the same position in the "inflate" state as it is in the "trapped volume" state, fluid in the pump feed 222 transported from the pump (and/or reservoir) flows in the same fashion as it does during the "trapped volume" state. In particular, fluid in the pump feed 222 flows into conduit 252 and then flows into the bottom of the second channel 244, which is fluidly connected to catheter feed 226 via aperture 254. As such, the fluid of the pump feed 222 flows into the catheter feed 226 for transport to the catheter balloon for inflation thereof.

Further, fluid in the central burette tube 220 (e.g., from the balloon fill media reservoir) flows from the central burette tube 220 to the pump return 224 by way of apertures 260 and 258. More specifically, as shown in FIG. 7, fluid in central burette tube 220 flows past the second plunger 248 towards the first channel 242 by flowing across the cross channel 245. The fluid from the central burette tube 220 enters the first channel 242 via aperture 260 which defines one end of the cross channel 245 (see FIG. 5). Because the first plunger 246 is in a downward position at the distal end of the first channel, the aperture 260 is in fluid communication with aperture 258. Accordingly, the fluid from the central burette tube 220 flows through aperture 260 into the first channel 242 and then into aperture 258, which empties into the pump return 224. Thus, the fluid of central burette tube 220 flows into the pump return 224 for transport to the pump.

Deflate Mode

Figure 8:
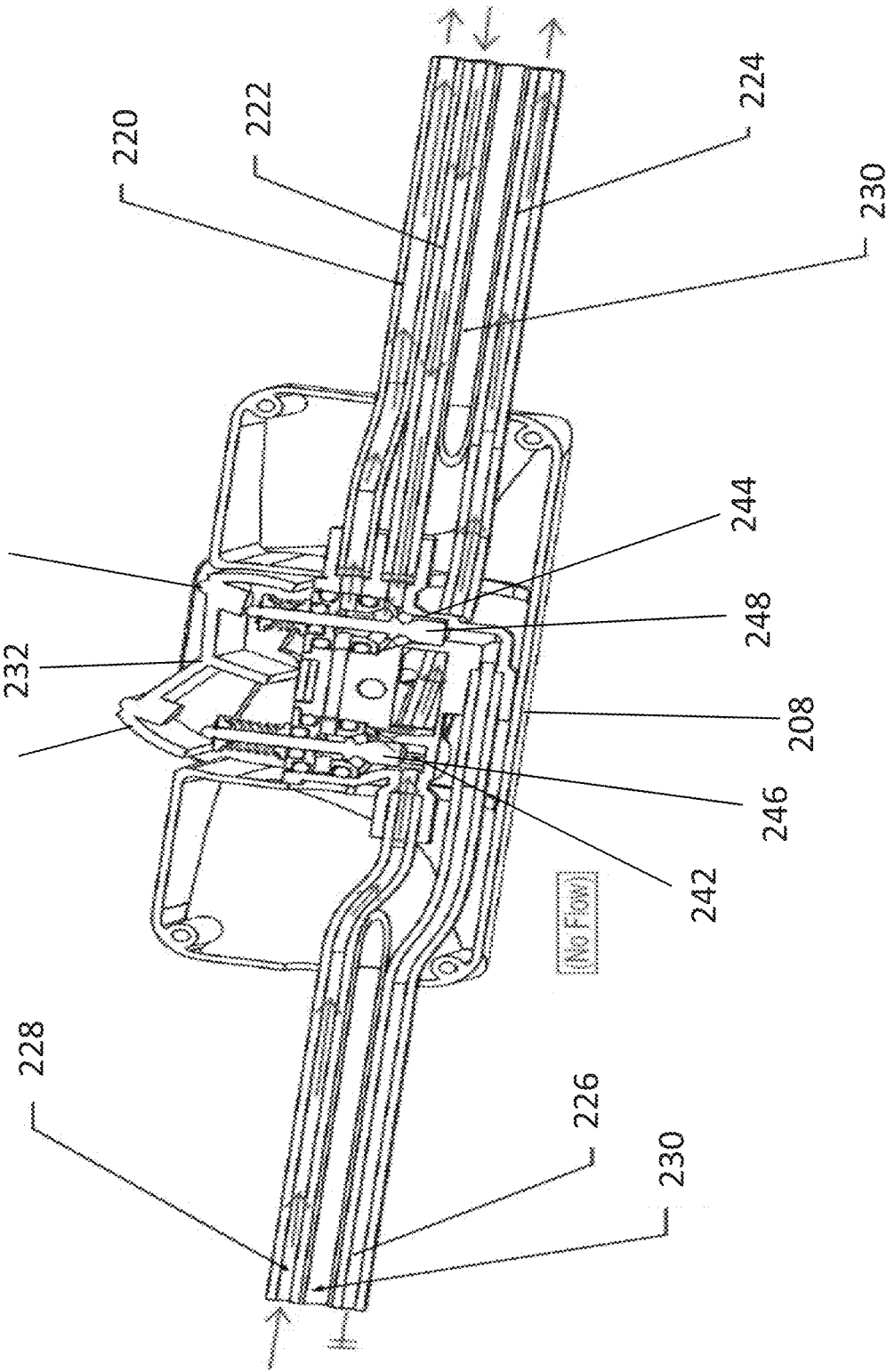

The flow of the liquid (e.g., fill media) during the "deflate" state for valve assembly 208 is shown in FIG. 8. With reference to FIGS. 5 and 8 and as mentioned above, in the "deflate" state the second end 236 exerts a downward force on the proximal end of the second plunger 248, causing a distal portion of the second plunger 248 to move to the bottom of the second channel 244. As such, the distal portion of the plunger 248 blocks aperture 254, thereby preventing any fluid in the pump feed 222 from transferring to the catheter feed 226. The fluid from pump feed 222 is instead re-routed to the central burette tube 220 via aperture 260. More specifically, because the second plunger 248 blocks aperture 254, fluid from the pump feed 222 empties into and fills up an upper portion of second channel 244. Once the fluid entering the second channel 244 reaches the height of aperture 262, it begins to enter aperture 262, which connects to the central burette tube 220. Accordingly, as the fluid enters aperture 262, the fluid then flows into central burette tube 220 for transport to the balloon fill media reservoir. It will be appreciated as fluid enters the second channel 244 from pump feed 222, the fluid can also flow into the cross channel 245 and flow to the first channel 242; however, the position of the plunger 246 in the first channel 242 and in particular, the o-ring 250 associated therewith blocks flow into the opening 258. Thus, fluid can only flow from the pump feed 222 into the central burette tube 220 during inflation.

Because the first plunger 246 is in substantially the same position in the "deflate" state as it is in the "trapped volume" state, fluid in the catheter return 228 is transported to the pump return 224 in the same fashion as it does during the "trapped volume" state. Specifically, the fluid returning from the catheter in catheter return 228 empties into the bottom portion of first channel 242 via aperture 256. Once there is enough fluid to fill the bottom portion of first channel 242, the fluid reaches the height of aperture 258 and begins to enter aperture 258, which empties into pump return 224.

Accordingly, as the fluid enters aperture 258, the fluid then flows into pump return 224 for transport to the pump.

Figure 9:
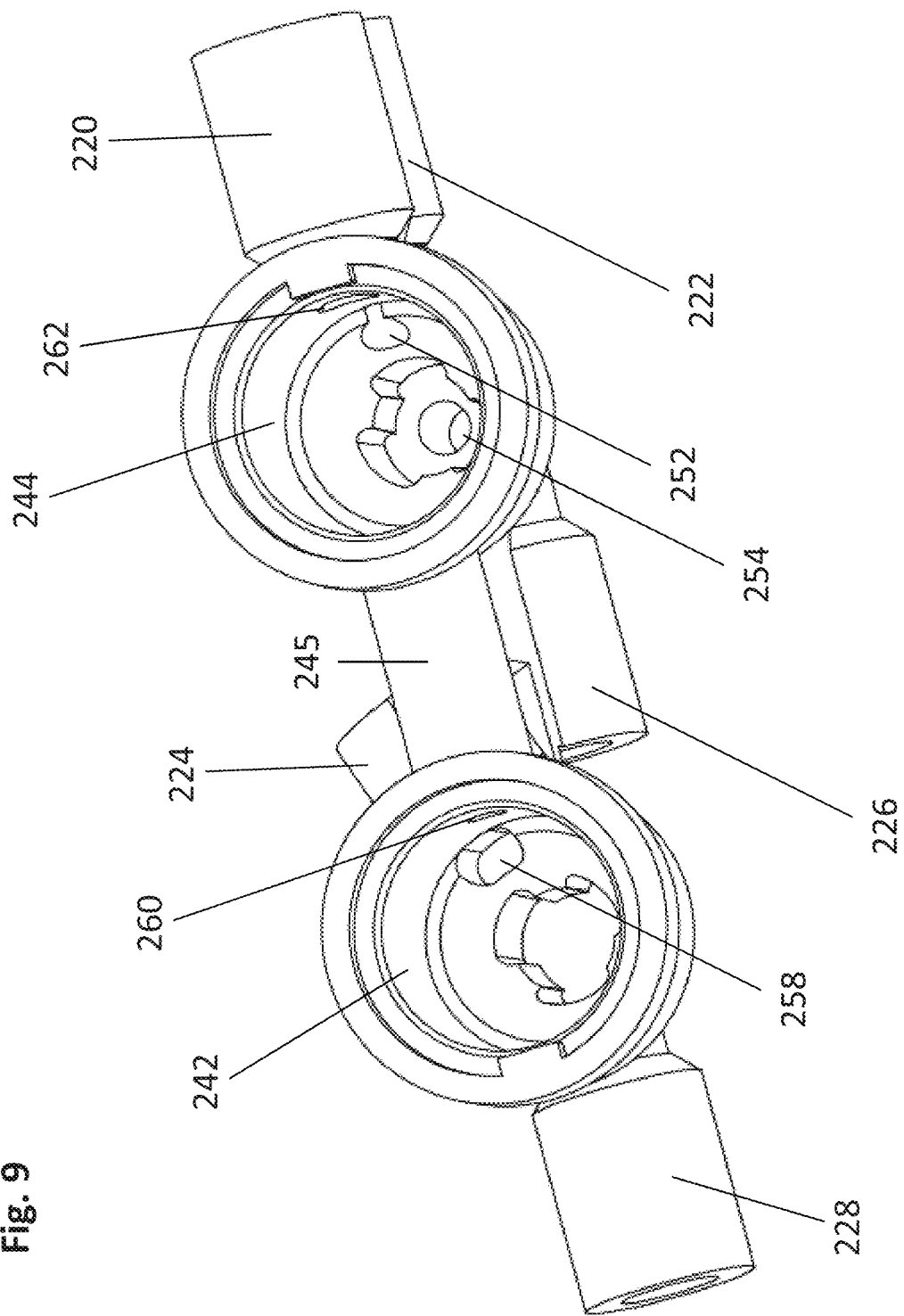
Figure 10:
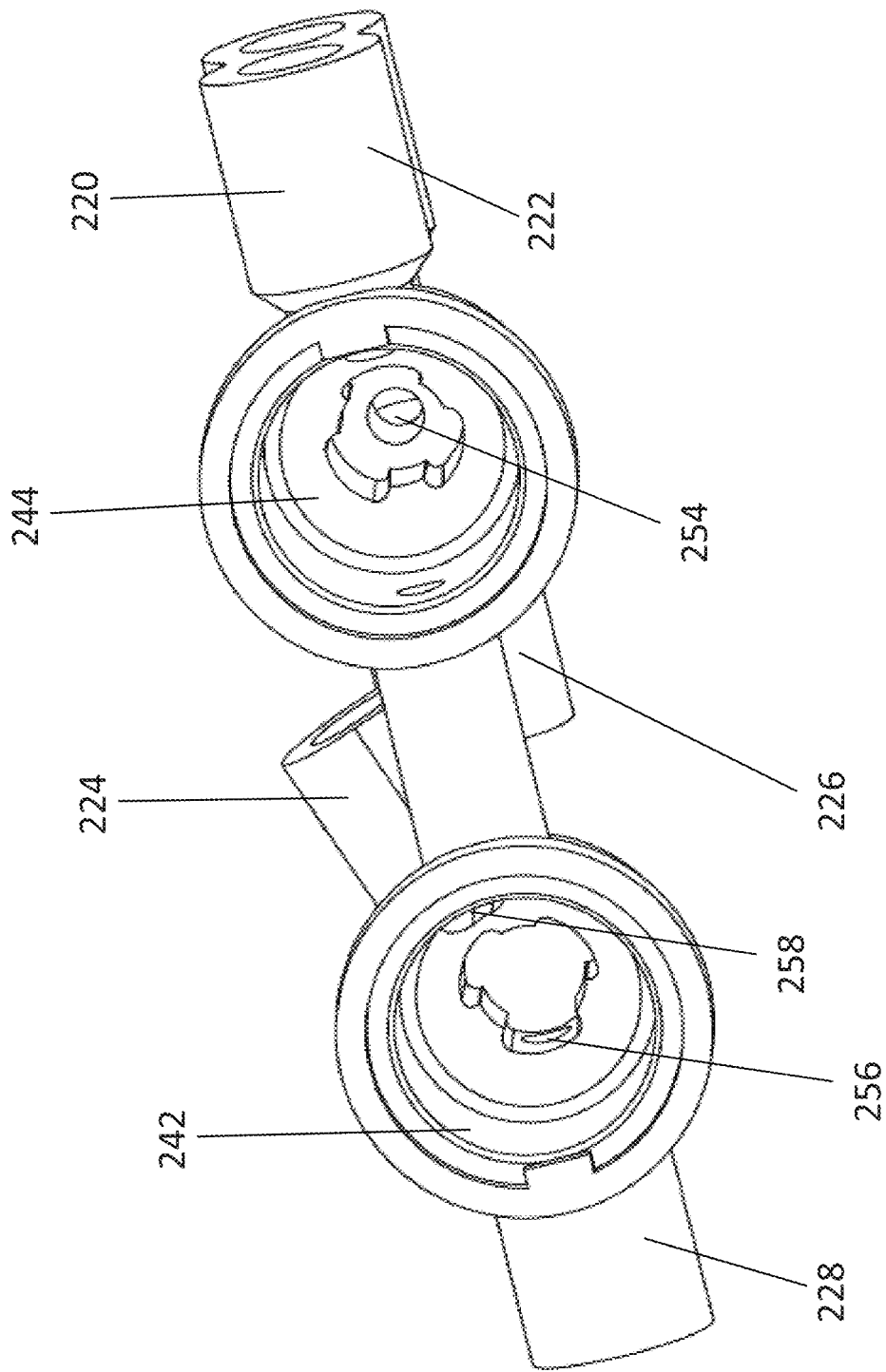
Figure 11:
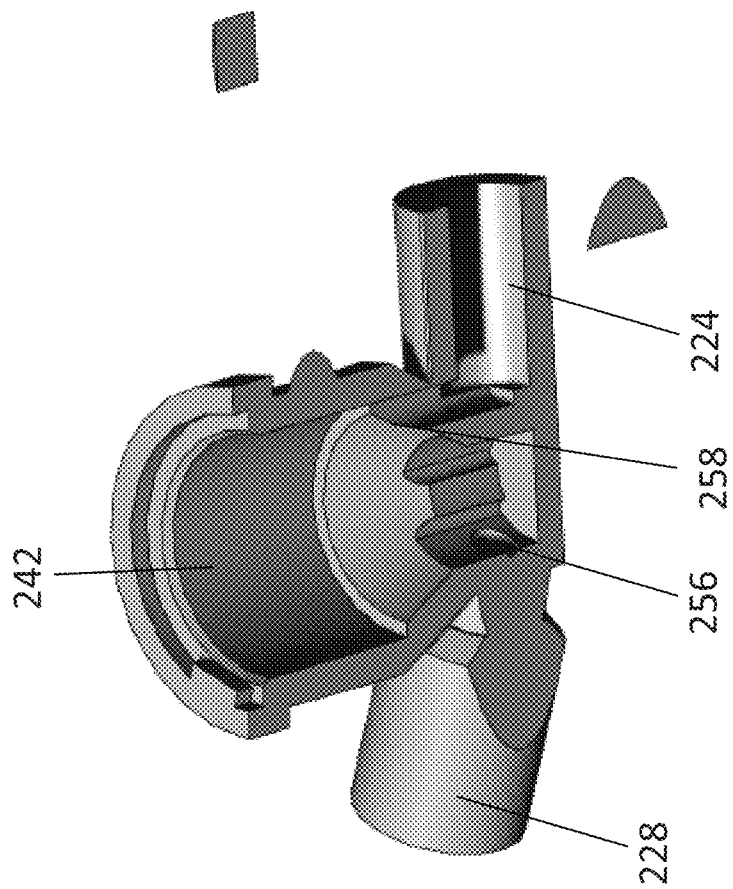
FIG. 11 shows a cross-sectional view of a channel of the exemplary valve housing body of the rocker valve assembly in accordance with one or more embodiments.

FIGS. 9-10 show various top and top perspective views of an exemplary valve housing body including first channel 242 and second channel 244 without their respective plungers, as well as the connections between the channels 242, 244 and the various fluid-containing tubes (e.g., central burette tube 220, pump feed 222, pump return 224, catheter feed 226, catheter return 228) as discussed above with regards to FIGS. 5-8. FIG. 11 shows a cross-sectional view of an exemplary first channel 242 and its connection to catheter return 228 and pump return 224.

Figure 12:
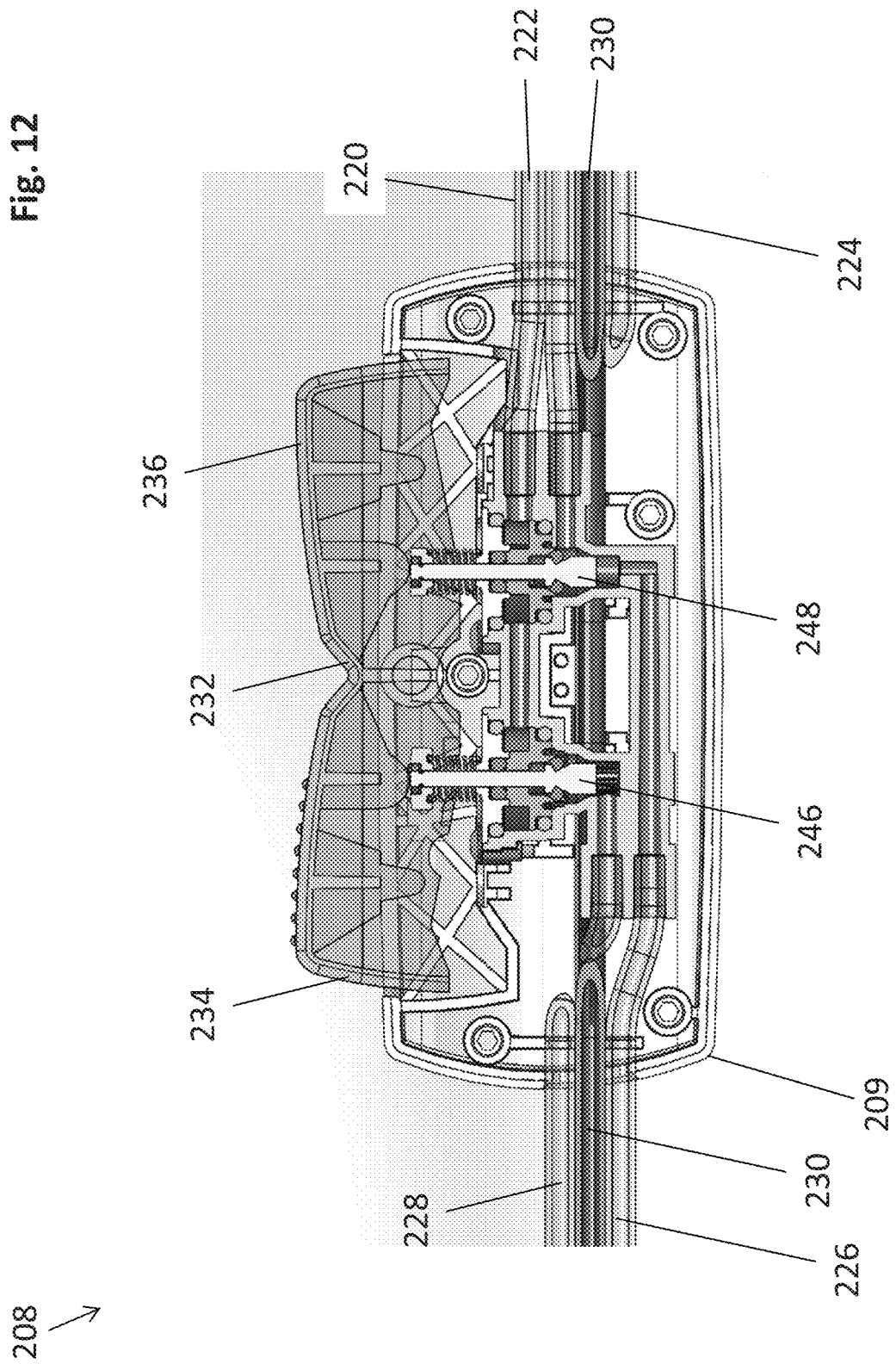
FIG. 12 shows a side cross-sectional view of an implementation of the rocker valve assembly in the trapped volume mode in accordance with one or more embodiments.

FIGS. 12-18 show various views of another implementation of the rocker valve assembly 208 as part of the system 200. FIG. 12 shows a side cross-sectional view of the rocker valve assembly 208 including exterior housing 209 and the rocker switch 232 of the rocker valve assembly 208. As shown in FIG. 12, the first end 234 of the rocker switch 232 has a texture such as ribs on the surface (which is pressed by the user) such that one end of the rocker switch 232 can be distinguished from the other end by touch alone without the user needing to look at the rocker button or valve housing. In this way, the user can determine which side of the rocker switch 232 to press to accomplish the desired actions without needing to look away from the console showing the endoscopic image being transmitted from inside of the balloon. Graphic indica can also be present on the housing as shown.

Figure 13:
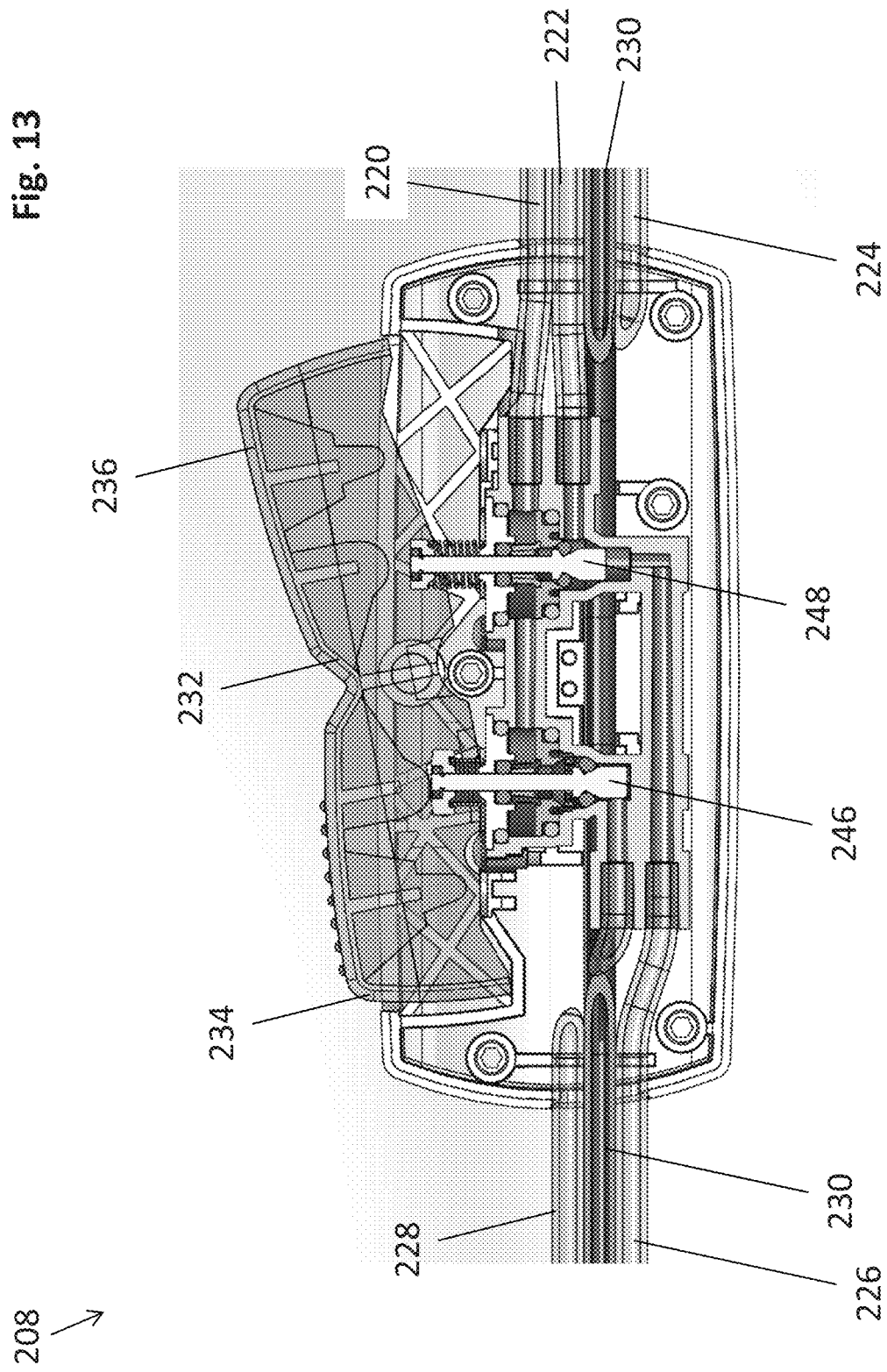
FIG. 13 shows a side cross-sectional view of an implementation of the rocker valve assembly in the inflate mode in accordance with one or more embodiments.
Figure 14:
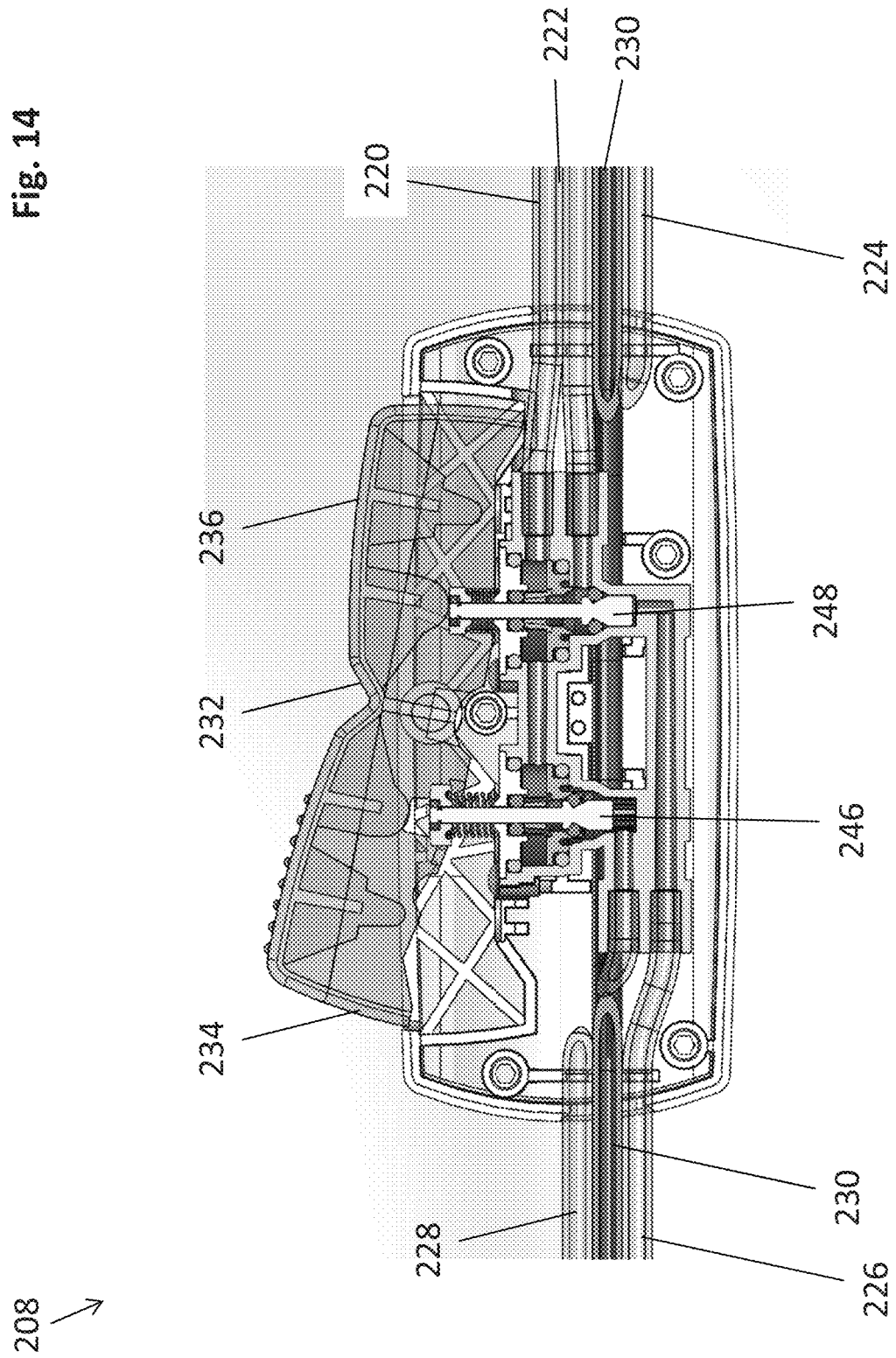
FIG. 14 shows a side cross-sectional view of an implementation of the rocker valve assembly in the deflate mode in accordance with one or more embodiments.
Figure 15:
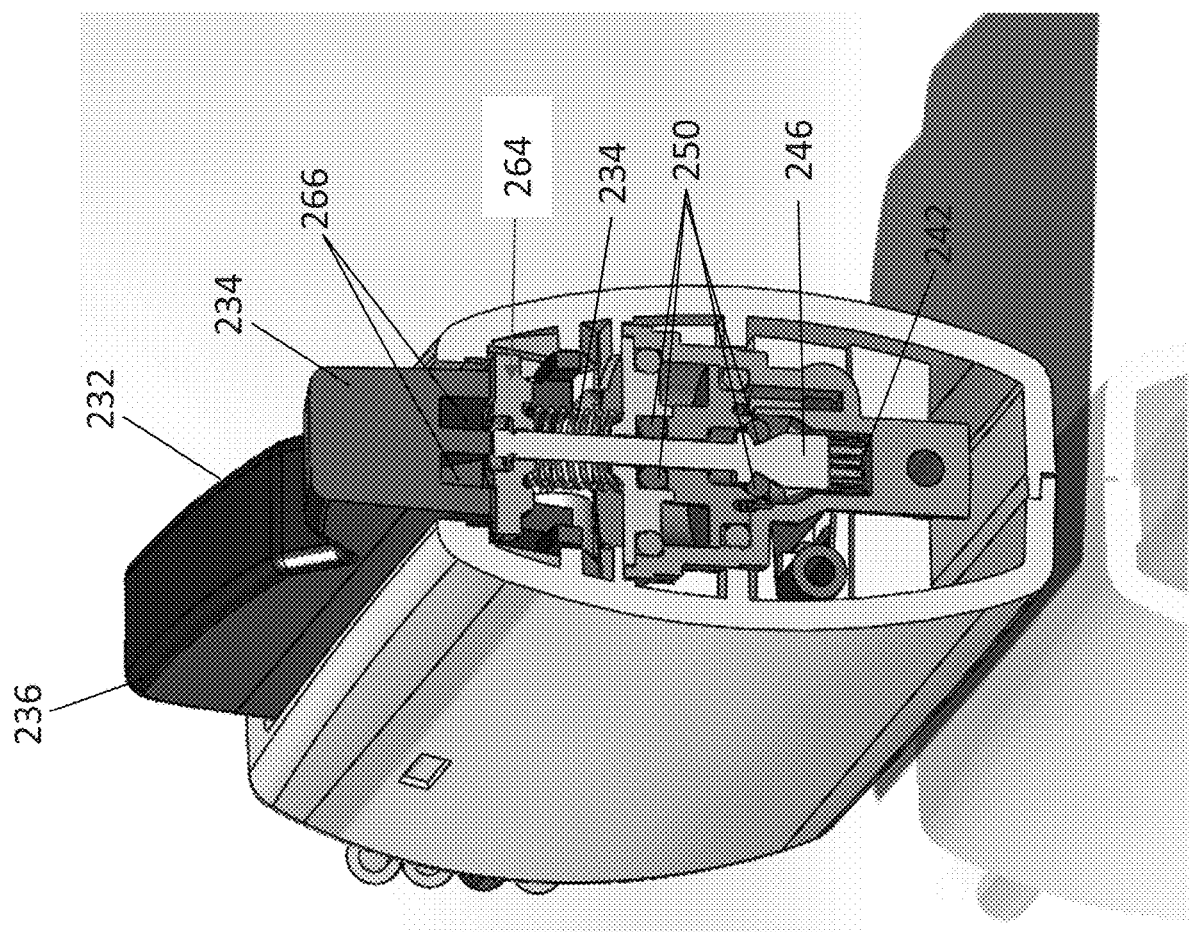
FIG. 15 shows another cross-sectional view of the rocker valve assembly in the trapped volume mode in accordance with one or more embodiments.
Figure 16:
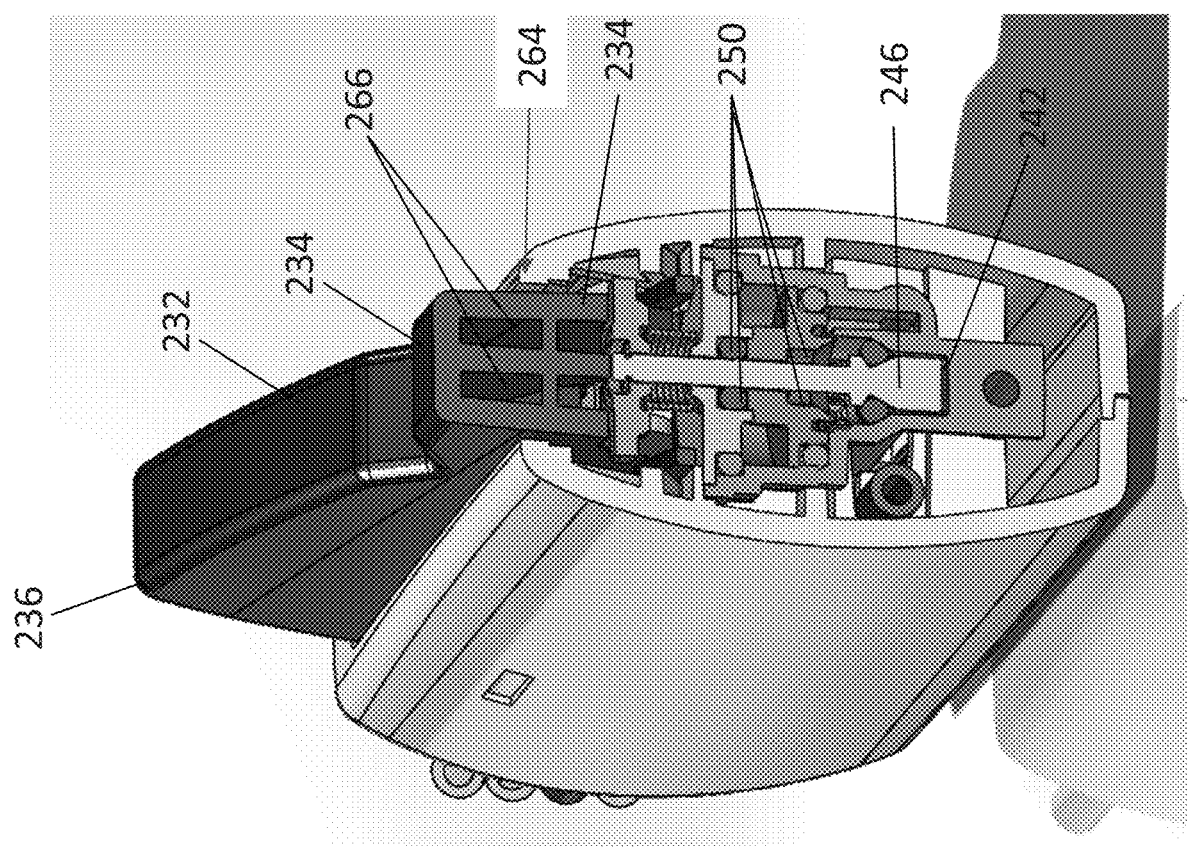
FIG. 16 shows another cross-sectional view of the rocker valve assembly in the inflate mode in accordance with one or more embodiments.
Figure 17:
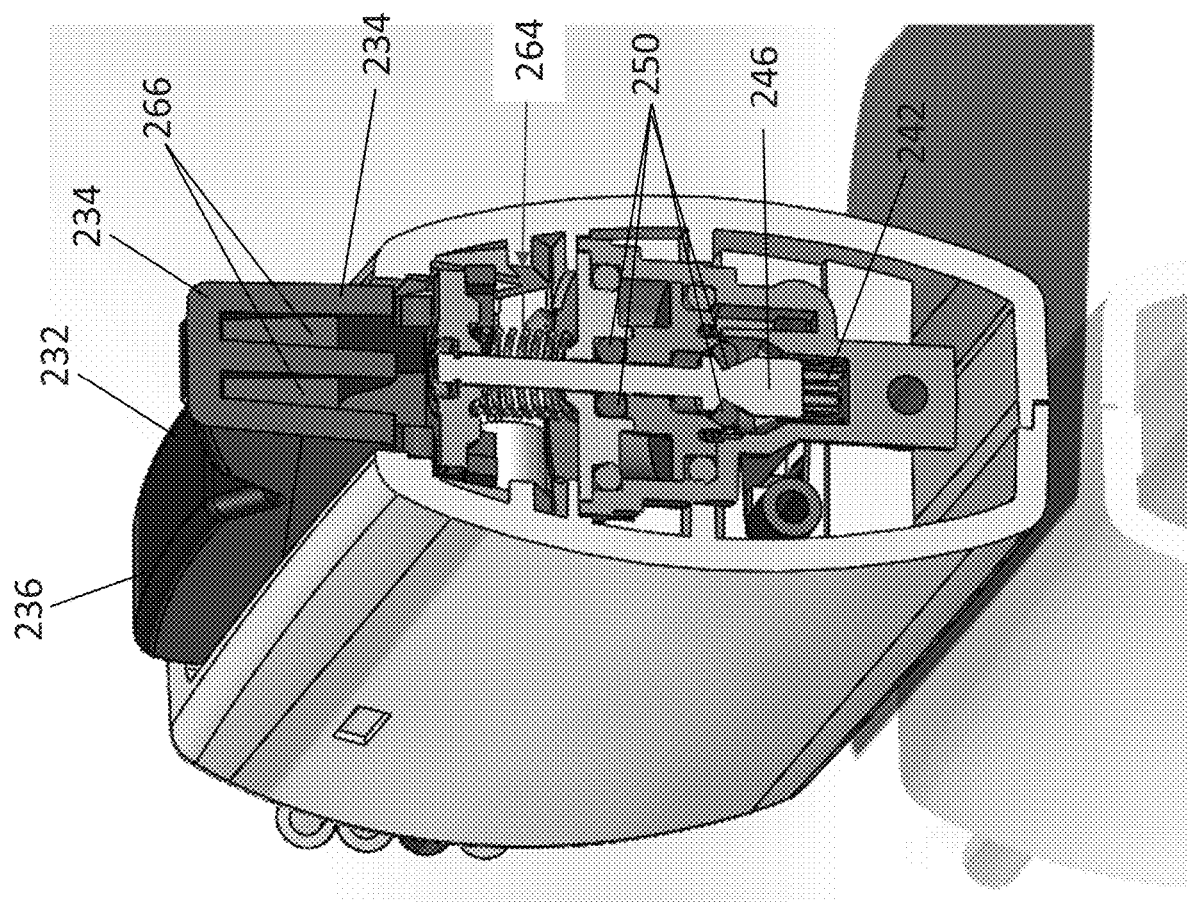
FIG. 17 shows another cross-sectional view of the rocker valve assembly in the deflate mode in accordance with one or more embodiments.

FIGS. 12-14 show side cross-sectional views of the interior of the rocker valve assembly 208 when the rocker switch 232 is in the "trapped volume" state (FIG. 12), the "inflate" state (FIG. 13), and in the "deflate" state (FIG. 14). FIGS. 15-17 shows cross-sectional views of the rocker valve assembly 208 of FIG. 12, which aligns with the vertical axis of the first plunger 246. In particular, FIG. 15 shows the cross-sectional view when the rocker valve assembly 208 is in the "trapped volume" state, FIG. 16 shows the cross-sectional view when the rocker valve assembly 208 is in the "inflate" state, and FIG. 17 shows the cross-sectional view when the rocker valve assembly 208 is in the "deflate" state.

A possible failure mode of the rocker valve assembly 208 is one in which the first plunger 246 remains stuck in the down position (i.e., stuck in "inflate" mode) after the user releases the first end 234 of the rocker switch 232. If this failure were to occur, then the balloon catheter would inflate to its maximum size. The maximum size is determined by the volume of balloon fill media in the reservoir. In one or more embodiments, the reservoir can be configured to have a fluid level sensor and the system 200 is configured such that when the level of media in the reservoir reaches a minimum level, the volumetric pump automatically stops to prevent further inflation of the balloon catheter. Even with this failsafe mechanism on the maximum size of the balloon catheter, in one or more embodiments an additional mechanism is provided to limit the possibility of continuous balloon inflation due to the first plunger 246 being stuck in the downward ("inflate") position.

Figure 18:
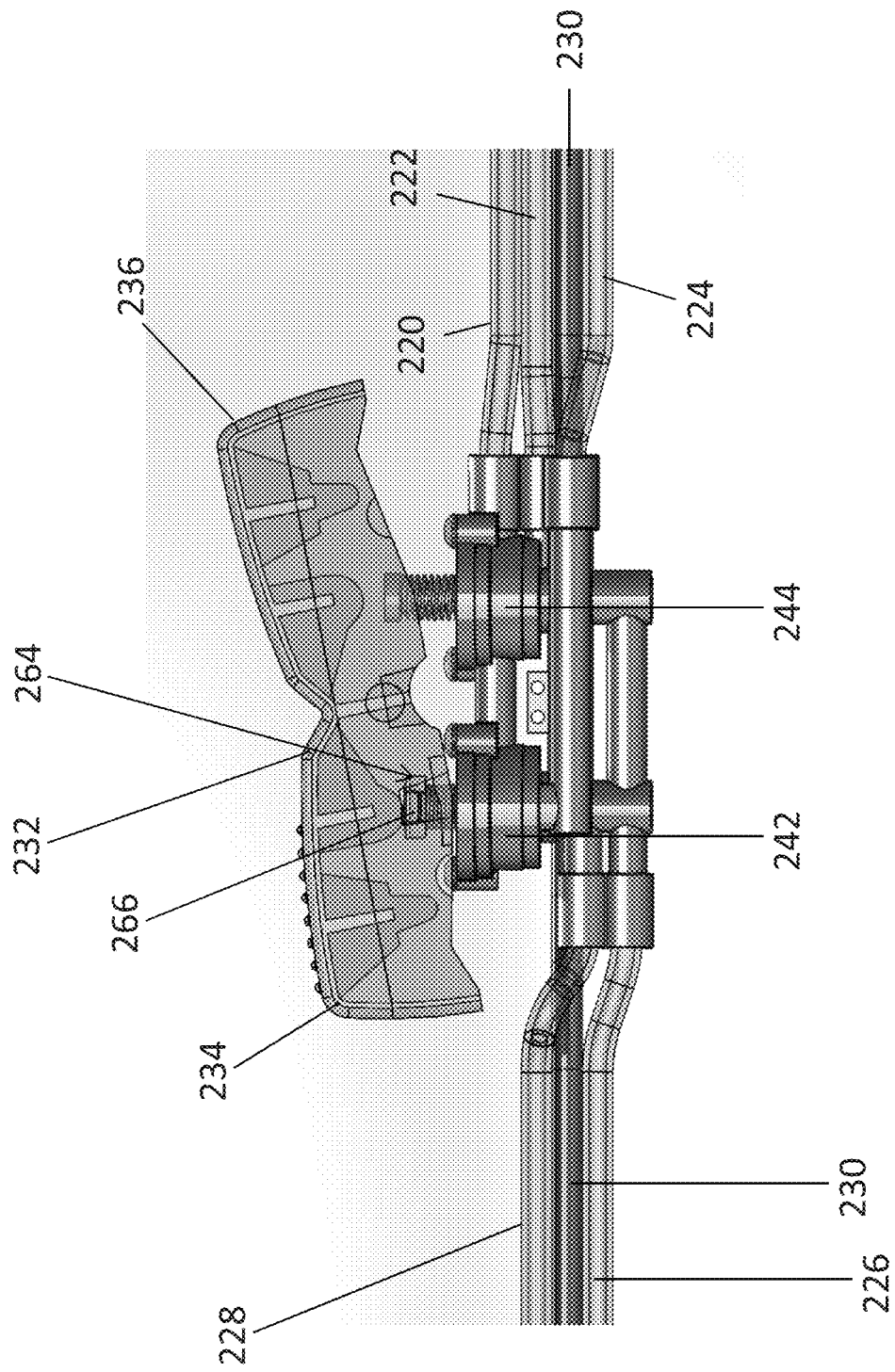
FIG. 18 shows a side view of the rocker valve switch and its connection to the various fluid-containing tubes in accordance with one or more embodiments.

In particular, in accordance with at least one embodiment, and as shown in FIGS. 15-17, the first plunger 246 can be connected to a component 264. The component 264 is generally rectangular and the outer lateral ends of component 264 penetrate the sidewalls of the first end 234 of the generally hollow rocker switch 232. Penetration of the sidewalls of the first end 234 can be facilitated by elongated holes in the sidewalls of the first end 234 as shown in FIGS. 15-17. One of the elongated holes 266 is also shown in FIG. 18, which shows a side view of the rocker switch 232 and its connection to the various fluid-containing tubes. The elongated holes 266 in the sidewalls of the first end 234 of the rocker switch 232 have a vertical extent that is larger than the vertical extent of component 264.

As can be seen in FIG. 15, the geometry of component 264 and the geometry of the elongated holes 266 in the sidewalls of the rocker switch 232 are configured such that if the first plunger 246 is stuck in the down position and the rocker switch 232 is centered in the "trapped volume" mode position, component 264 is positioned at the lowermost portion of the elongated hole 266 in the sidewall of the rocker switch 232. Moving the rocker switch 232 to the "deflate" mode (see FIG. 17) moves the elongated holes 266 in the sidewall of the first end 234 of the rocker switch 232 upward relative to the first plunger 246 and also upward relative to component 264. Such motion of the rocker switch 232 will consequently move component 264 upward and with it the first plunger 246. In this manner, moving the rocker switch 232 into the "deflate" position forces the first plunger 246 out of the downward position and back into the correct position for deflation of the balloon catheter. However, if the first plunger 246 is not stuck in the downward position and instead it is positioned in the up position and the rocker switch 232 is in the centered "trapped volume" position, then component 264 is now positioned at the uppermost portion of the elongated hole in the sidewall of first end 234 the rocker switch 232 (see FIG. 15). Moving the rocker button to the deflate position will move the elongated holes 266 in the sidewall of the first end 234 upward relative to component 264 such that component 264 is not affected by the motion of the rocker switch 232 (see FIG. 17). Moving the rocker switch 232 to the deflate position will simply reposition the elongated hole 266 relative to component 264 so that component 264 is now in the lowermost portion of the elongated hole 266.

In one or more embodiments, the mechanism described above to prevent a stuck first plunger 246 from causing continuous inflation of the balloon catheter can also be used on the second plunger 248 of the valve assembly 208 to prevent continuous deflation of the balloon catheter.

Sliding Tube Valve Embodiment

FIGS. 19-23 display another embodiment of the balloon fill media control system (system 300) that similarly comprises a valve assembly having a "trapped volume" state, an "inflate" state, and a "deflate" state. Like systems 100 and 200 described above, the valve assembly of system 300 can be placed in one of these three states by the operator. As such, the circulation of the balloon fill media in system 300 during the three "states" is substantially the same as the circulation of balloon fill media described in reference to the above embodiments, except with regards to how the fill media passes through the valve assembly, as discussed in further detail below.

It will therefore be appreciated that the valve assembly of FIGS. 19-23 can be a substitute for valve 108 and thus placed at the location of valve 108 in FIG. 1.

Figure 19:
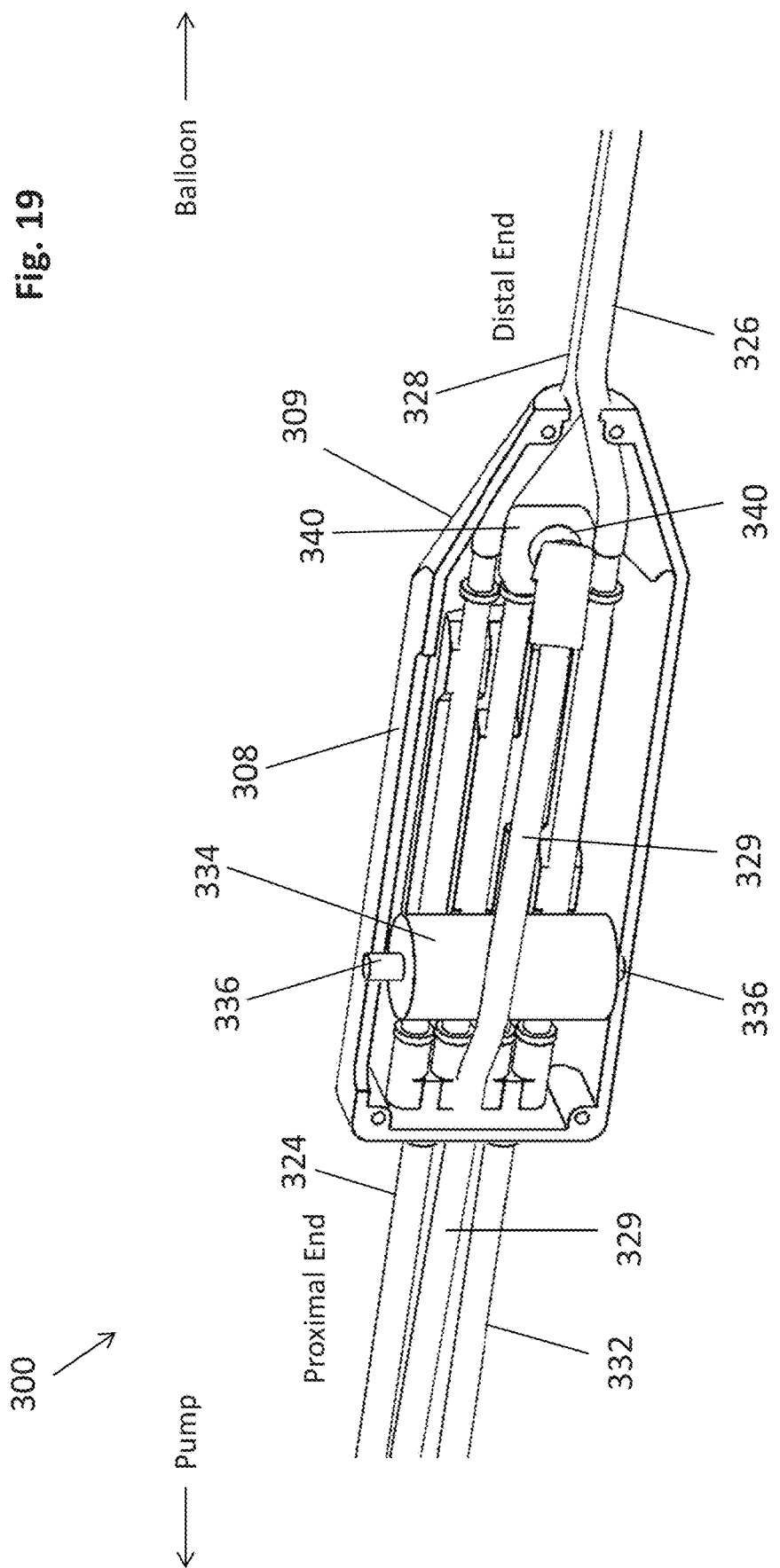
FIG. 19 shows a side perspective view of a sliding tube valve embodiment of the balloon fill media control system in accordance with one or more embodiments.

FIG. 19 displays a side perspective view of a portion of the balloon fill media control system 300. Like systems 100 and 200 described above, the system 300 can include a balloon catheter, a balloon fill media reservoir having a fill port, a volumetric pump, a vacuum relief valve and an air separator substantially as shown in system 100 (FIGS. 1-3). The system 300 also comprises a sliding tube valve assembly 308 having a housing 309 (corresponding half of housing 309 not shown to show interior of valve assembly 308). As mentioned above, the sliding tube valve assembly 308 has a "trapped volume" state, an "inflate" state, and a "deflate" state. As shown in FIG. 19, the system 300 also comprises a number of tubes, including a pump feed 322, a first pump return 324, a catheter feed 326, a catheter return 328, and a second pump return 329. The tubes are configured to circulate fluid (e.g., balloon fill media) through the system 300. The system 300 can further comprise at least one illumination fiber 330, as shown in FIG. 20, which can be used in conjunction with an endoscope to determine whether contact has been achieved between the balloon catheter and the target tissue in the body of the patient.

Figure 20:
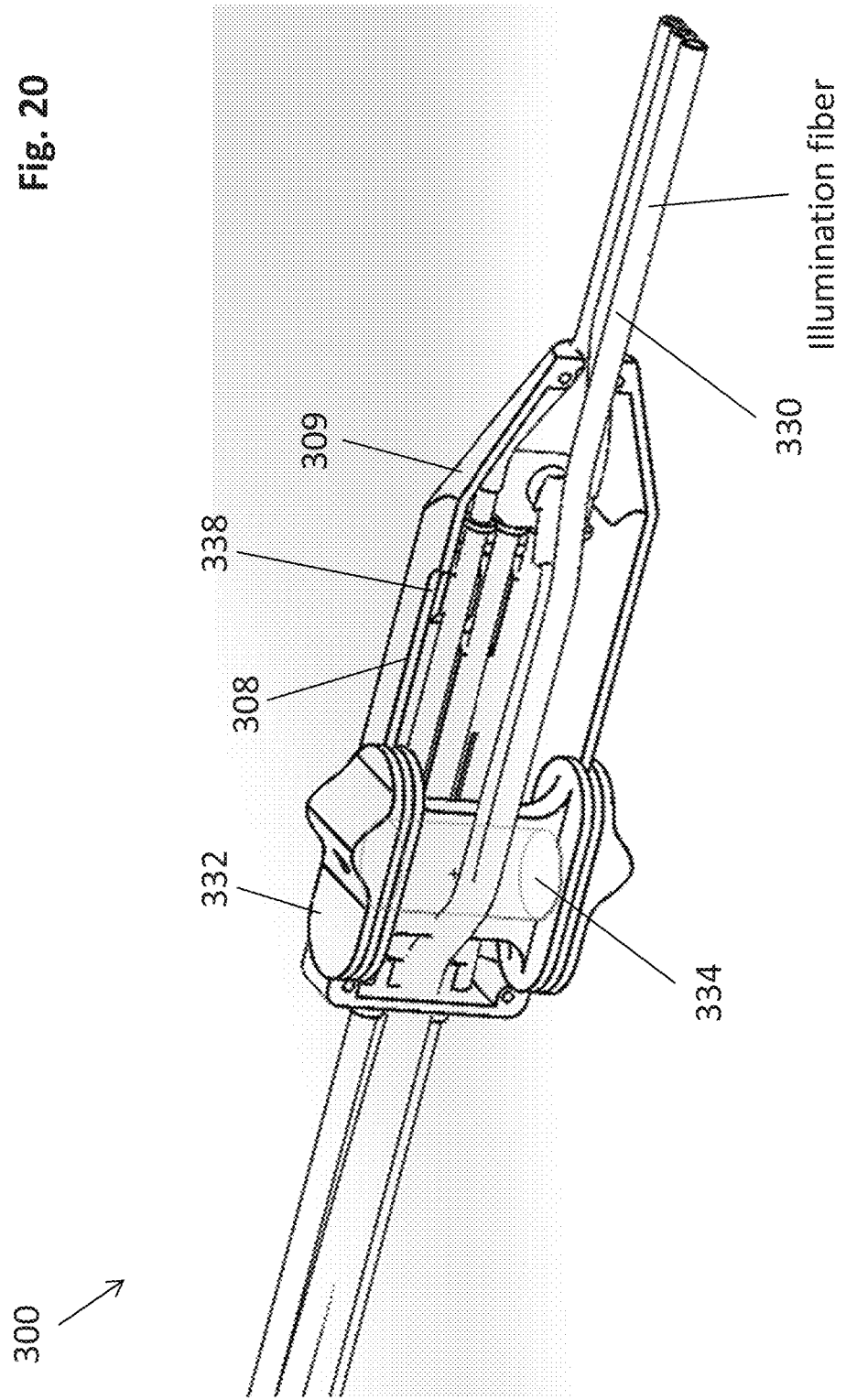
FIG. 20 shows a side perspective view of the sliding tube valve embodiment of the balloon fill media control system, including an illumination fiber, in accordance with one or more embodiments.

With reference to FIGS. 19-20, the sliding tube valve assembly 308 features a slider lever 332 having handles on one or both sides of the housing 309 and a sliding member (roller) 334 that is located within the housing operatively connected to the slider lever 332 one or both ends 336 of the sliding member 334, where the slider lever 332 is the actuation mechanism for selectively moving the sliding tube 334 between a "sterilization" state, a "trapped volume" state, an "inflate" state, and a "deflate" state. For example, in the embodiment as shown in FIG. 20, the slider lever 332 is configured to move along a track 338, thereby moving the sliding member 334 to one of four positions within the assembly 308 that correspond to the sterilization" state, "trapped volume" state, "inflate" state, and "deflate" state, respectively.

Figure 21:
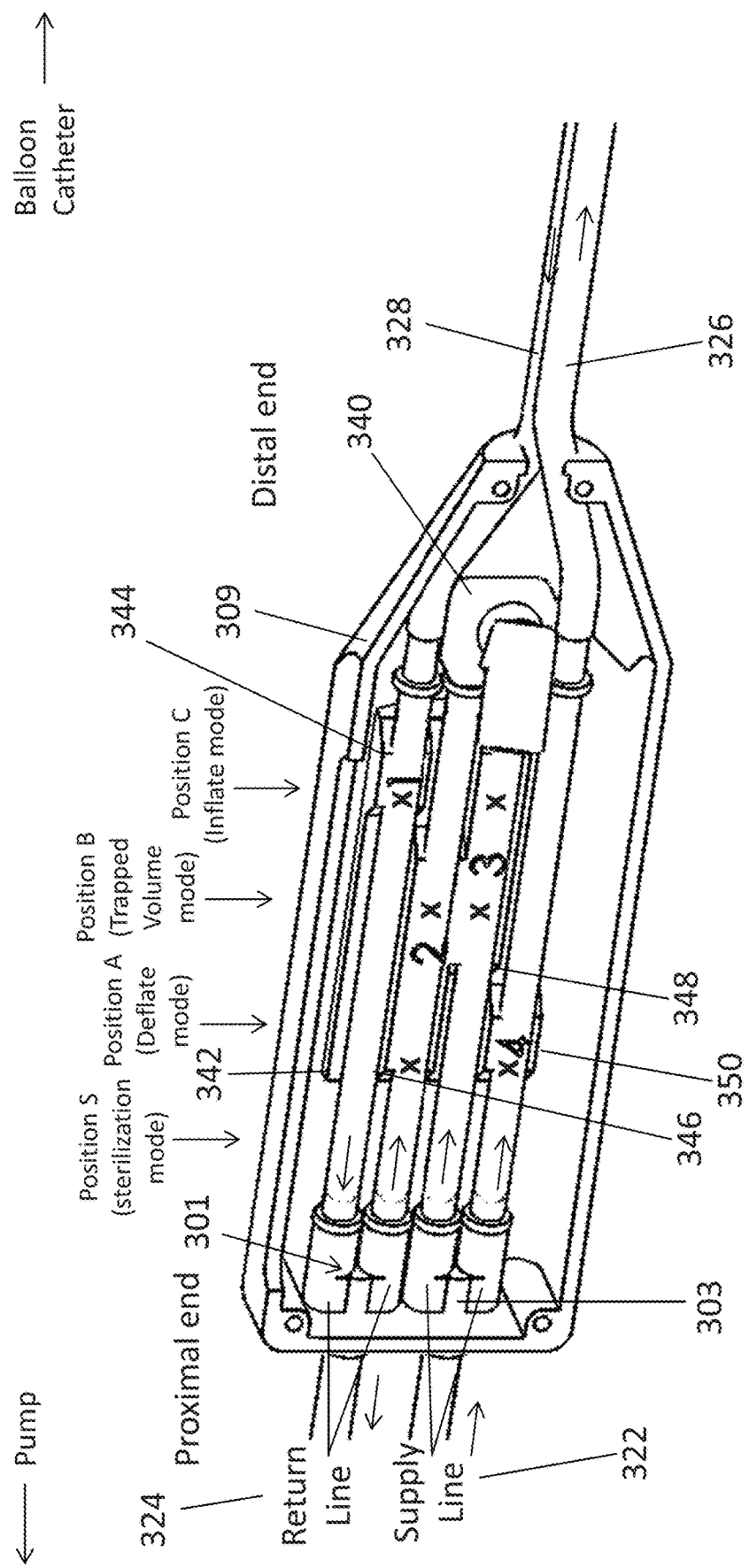
FIG. 21 shows a side perspective view of the inside of an embodiment of the sliding tube valve assembly showing four positions for the sliding member in accordance with one or more embodiments.
Figure 22:
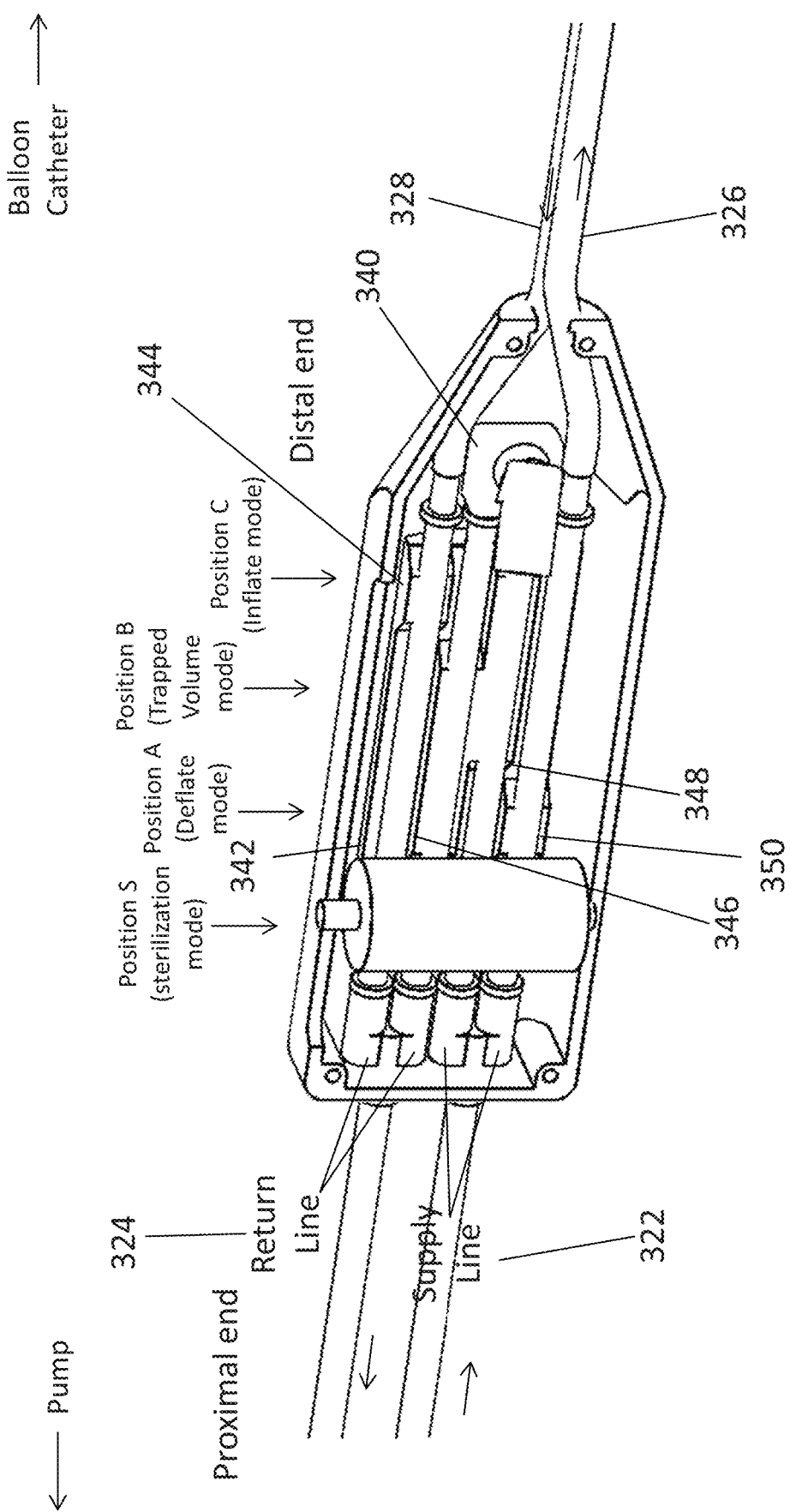
FIG. 22 shows a side perspective view of the inside of an embodiment of the sliding tube valve assembly in which the sliding member is in sterilization mode in accordance with one or more embodiments.
Figure 23:
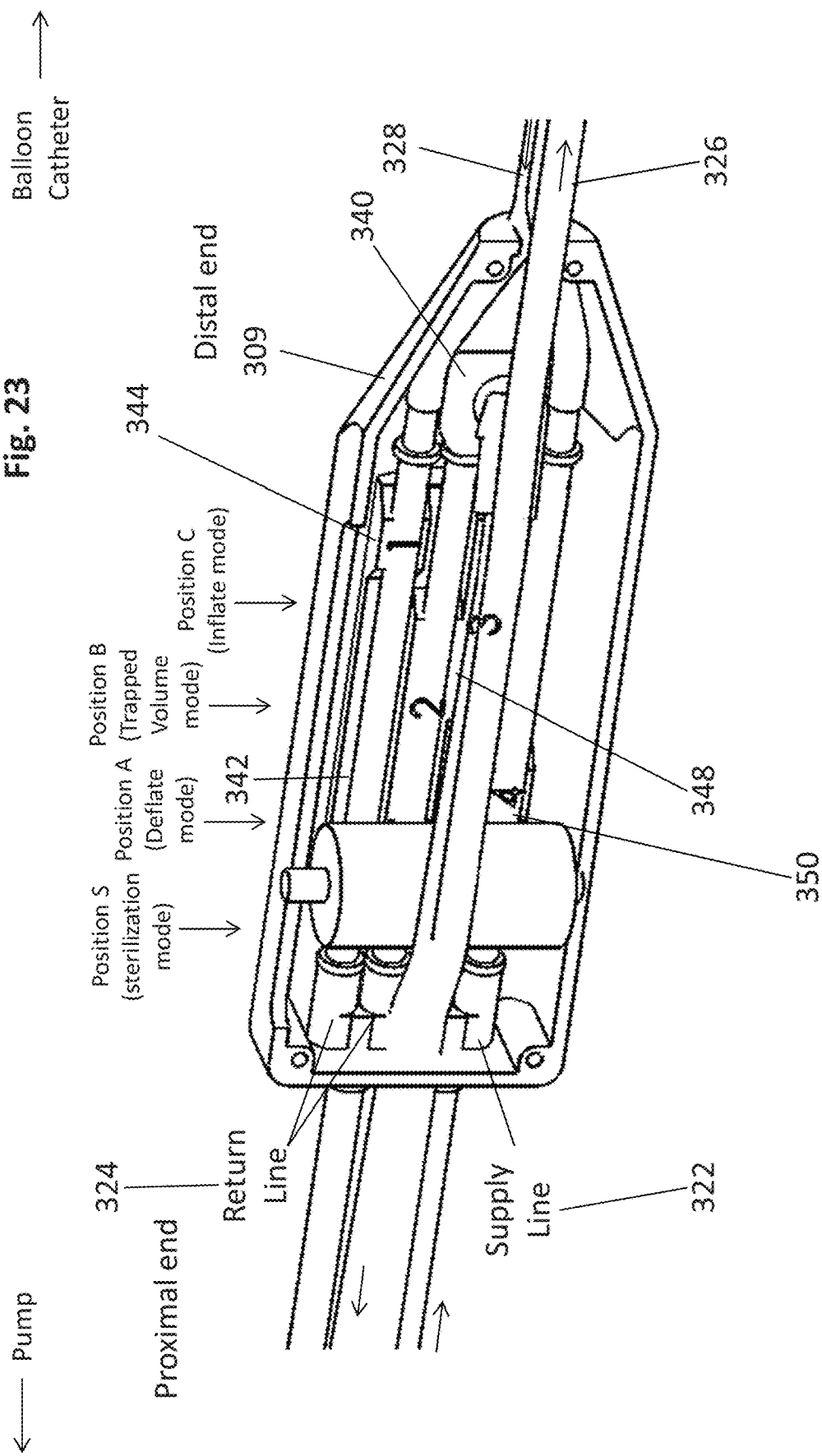
FIG. 23 shows another side perspective view of the inside of an embodiment of the sliding tube valve assembly in which the sliding member is in sterilization mode in accordance with one or more embodiments.

FIGS. 21-23 show side perspective views of the inside of an embodiment of the sliding tube valve assembly 308 showing the four positions for the sliding member. In particular, as shown in FIGS. 21-23, the sliding member can be moved (via the slider lever 332) to a position "S" (sterilization mode), a position "A" (deflate mode), a position "B" (trapped volume mode), and a position "C" (inflate mode). Position "S" is located at a proximal end of the assembly 308 (i.e., adjacent to pump feed 322 and pump returns 324 and 329). Position "A" is at a location distal to position "S" and proximate to position "B." Position "B" is at a location proximate to position "C", and position "C" is located at a distal end of the assembly 308 (i.e., adjacent to the catheter feed 326, a catheter return 328).

FIG. 21 also shows various tubes (tubes "1", "2", "3", and "4") within the housing 309 that are in fluid connection with the conduits (i.e., pump feed 322, first pump return 324, catheter feed 326, catheter return 328, and second pump return 329) transporting fluid (e.g., balloon fill media) between the balloon catheter and the pump. Tubes "1", "2", "3", and "4" can be made of a flexible material such as silicone. It will also be understood that tubes 1, 2, 3, and 4 can be an integral part of the respective conduits 322, 324, 326, 328, respectively. As shown in FIGS. 19 and 21, tube "1" receives fluid from catheter return 328 and then transfers the fluid to first pump return 324 and/or tube "2". In other words, tubes "1" and "2" and first pump return 324 are fluidly connected (e.g., via a Y-shaped connector 301 (FIG. 21)) such that fluid from tube "1" can flow into first pump return 324 and/or tube "2." Tube "2" is capable of receiving fluid from tube "1" and then is configured to transfer the fluid to the hollow connector space 340. Tube "4" receives fluid from pump feed 322 and then transfers the fluid to catheter feed 326. Tube "3" also receives fluid from pump feed 322, but then is configured to transfer the fluid to a hollow connector space 340. In other words, pump feed 322 is fluidly connected to tubes "3" and "4" (e.g., via a Y-shaped connector 303 (FIG. 21)) such that fluid from pump feed 322 can flow into tube "3" and/or tube "4."

The hollow connector space 340 is in fluid connection with tubes "2" and "3," as well as second pump return 329. As such, when fluid is received in the hollow connector space 340 (from tubes "2" and/or "3"), the negative pressure created by the pump (when the pump is operating) draws the fluid from the connector space 340 into second pump return 329 for transport to the pump.

With continued reference to FIG. 21, the assembly 308 further includes a surface 342 located between the tubes and one side of the housing 309. The surface includes four raised portions 344, 346, 348, and 350 having varying lengths and each extending along and abutting one of the tubes. In one or more alternative implementations, the surface 340 can be replaced with four surfaces, each one consisting of one the raised portions 344-350.

The raised portions 344-350 can thus be thought of as being rails that are parallel to one another and in stacked arrangement along the side wall of the housing. The raised portions of the rails are offset from one another as shown.

As shown in FIG. 21, the raised portion 344 abuts tube "1" at position "C." Raised portion 346 is longer than raised portion 344 and abuts tube "2" along positions "A" and "B." Raised portion 348 is approximately the same length as raised portion 346, and it abuts tube "3" along positions "B" and "C." Raised portion 350 is approximately the same lengthy as raised portion 344, and it abuts tube "4" at position "A" only. None of the raised surfaces 344-350 are located along position "S." As the sliding member 334 is moved between positions "S", "A", "B", and "C", the flow of the liquid (e.g., balloon fill media) through the tubes of the assembly changes as discussed in greater detail below.

Sterilization Mode

When the sliding member 334 is in its most proximal location (i.e., location most proximal to pump feed 322 and pump return 324), the sliding member 334 is in position "S" or "sterilization mode." In sterilization mode, all of the tubes (tubes "1-4") are open such that a sterilizing fluid (e.g., gas or liquid) can pass through all of the tubes and conduits (324-329) freely to sterilize the system between uses. FIGS. 22 and 23 show the sliding member 334 in position "S," in which tubes "1-4" remain open. FIG. 22 shows the assembly 308 in sterilization mode, but the second pump return 329 and illumination fiber 330 are not shown to fully show the raised portions 348 and 350. FIG. 23 shows the assembly 308 in sterilization mode showing the second pump return 329 and illumination fiber 330, where the second pump return 329 and illumination fiber 330 obscure the raised portions 348 and 350 from view. In FIG. 21, slider member (roller) 334 (not shown) is not positioned adjacent any of the raised portions 344-350, thus all conduits are open.

Deflate Mode

With continued reference to FIGS. 21 and 22, when the sliding member 334 is in its second most proximal location, the sliding member 334 is in position "A" or "deflate mode." In deflate mode, tube "2" is pinched between the sliding member 334 and the raised portion 346 and tube "4" is pinched between the sliding member 334 and the raised portion 350. As such, in deflate mode, fluid is prevented from flowing through tubes "2" and "4" as these tubes are pinched shut at position "A." FIG. 21 shows the approximate locations ("x") at which tubes "2" and "4" are pinched in position "A" (deflate mode).

Like the systems 100 and 200 discussed above, when system 300 is in deflate mode, fluid is removed from the balloon catheter and substantially no fluid is transferred to the balloon catheter such that the balloon catheter begins to deflate. Thus, in deflate mode for system 300, fluid from catheter return 328 (coming from the catheter) flow into tube "1" and subsequently to pump return 324 for transport to the pump (and/or the balloon fill media reservoir). Because tube "2" is pinched in deflate mode, the fluid in tube "1" does not enter tube "2." The fluid from pump feed 322 (coming from the pump and/or reservoir) flows into tube "3," which empties into connector space 340. Due to the negative pressure created by the pump, the fluid in the connector space 340 is drawn from the connector space 340 into second pump return 329, for transport back to the pump and/or reservoir. Because tube "4" is pinched in deflate mode, fluid from pump feed 322 does not flow into tube "4" and thus no fluid is transferred to catheter feed 326 for transfer to the catheter.

Trapped Volume Mode

When the sliding member 334 is in its second most distal location, the sliding member 334 is in position "B" or "trapped volume mode." In trapped volume mode, tube "2" is pinched between the sliding member 334 and the raised portion 346 and tube "3" is pinched between the sliding member 334 and the raised portion 348. As such, in trapped volume mode, fluid is prevented from flowing through tubes "2" and "3" as these tubes are pinched shut at position "B." FIG. 21 shows the approximate locations ("x") at which tubes "2" and "3" are pinched in position "B" (trapped volume mode).

When system 300 is in trapped volume mode, the volume of fluid already circulating between the pump and the balloon catheter is "trapped" in a closed loop between the pump and the balloon catheter such that the balloon catheter remains inflated and does not become overheated during operation. Thus, in trapped volume mode for system 300, fluid from catheter return 328 (coming from the catheter) flow into tube "1" and subsequently to pump return 324 for transport to the pump. Because tube "2" is pinched in trapped volume mode, the fluid in tube "1" does not enter tube "2." The fluid from pump feed 322 (coming from the pump) flows into tube "4," which then flows into catheter feed 326 for transport to the catheter. Because tube "3" is pinched in the trapped volume mode, fluid from pump feed 322 does not flow into tube "3" and thus no fluid is transferred to second pump return 329.

Inflate Mode

When the sliding member 334 is in its most distal location (i.e., location most distal to pump feed 322 and pump return 324), the sliding member 334 is in position "C" or "inflate mode." In inflate mode, tube "1" is pinched between the sliding member 334 and the raised portion 344 and tube "3" is pinched between the sliding member 334 and the raised portion 348. As such, in inflate mode, fluid is prevented from flowing through tubes "1" and "3" as these tubes are pinched shut at position "C." FIG. 21 shows the approximate locations ("x") at which tubes "1" and "2" are pinched in position "C" (inflate mode).

When system 300 is in inflate mode, and is continuously pumped into the balloon catheter, but fluid is substantially prevented from flowing out of the balloon to the rest of the system, thereby increasing the size of the balloon catheter. Thus, in inflate mode for system 300, fluid from catheter return 328 (coming from the catheter) is prevented from flowing into tube "1" as tube "1" is pinched at position "C." As such, fluid is prevented from flowing into pump return 324 or tube "2." The fluid from pump feed 322 (coming from the pump and/or reservoir) flows into tube "4," which then flows into catheter feed 326 for transport to the balloon catheter to inflate the balloon. Because tube "3" is pinched in the inflate mode at position "C," fluid from pump feed 322 does not flow through tube "3" into connector space 340. Further, because no fluid is received in tube "2", substantially no fluid is received by connector space 340. Accordingly, substantially no fluid is transferred into second pump return 329.

Balloon Cooling Systems

In one or more embodiments, the present application discloses a cooling system that utilizes a single head peristaltic pump to circulate fluid as well as to create negative pressure in the burette (balloon fill media reservoir). FIG. 24 shows an exemplary configuration of the burette (reservoir) with peristaltic vacuum assist option. In this configuration, tube 1008 is in communication with fluid in the burette (reservoir) and FIG. 25 shows the cooling liquid part of the system in more details.

The vacuum system shown in FIG. 24 consists of peristaltic pump (silicone tubing) connected to tube 1007 so that negative (relative to atmospheric) pressure is created in tube 1007 when pump rotates in clockwise direction (direct). Check-valve 1001 helps to prevent pressure build-up in the burette when pump rotates counterclockwise (reverse) and it also helps to prevent pulsations of pressure in the burette. Air filter 1006 helps to prevent biocontaminants in the air from entering sterile environment of the burette. Hole 1009 is needed for fluid communication between internal sections of the burette. Check-valve 1004 and air filter 1005 are needed for balloon deflation stage. During this stage, liquid returns back into burette and compresses air in the head space. When this happens, valve 1004 opens and allows air to exit the burette. Air Filter 1005 prevents biocontaminants from entering the burette. Valve 1002 allows atmospheric air to enter the burette (through air filter 1003 to avoid contamination of the burette) when pressure difference between the burette environment and the external atmosphere riches the check pressure of the valve. This helps to keep pressure in the burette at constant level regardless of the rotational speed of the pump. This system helps to provide cooling of the balloon and maintaining the balloon pressure at gauge pressures down to zero, which allows one to use balloons made of very soft materials.

FIG. 25 shows flow diagram of the catheter with the burette operating in so called normal mode, where balloon pressure can be changed based on rotational speed of the peristaltic pump P1-P2 (same drive with two peristaltic tubes). In this mode, valve 2 is closed and valves 1 and 3 are open that allows fluid in the catheter to communicate with fluid in the burette (inflate/deflate). Additional valves 1-3 can be added to allow a system to operate in constant volume mode. When valves 1 and 3 are closed and valve 2 is open, cooling liquid has constant volume which helps to keep the balloon at the desired size by initially inflating it to this size and switching to the constant volume mode when the rotational speed of the pump does not affect the balloon pressure.

Valves 1-3 can be combined in a single block and operated with single lever that could switch between different operating modes as shown in FIG. 26. Valve design could use a number of different operating mechanisms. In a preferred configuration, the valve is based on pinched tubes, while in other configurations it can be trumpet valve or a stopcock type valve.

Mode Switch Valve

The following paragraphs describe exemplary configurations of the Mode Switching Valve, which works in a similar way as the valve shown in FIG. 26. FIG. 27 shows primary parts of one of the four valves of the mechanism 400 described in this disclosure. Tube 408 is a segment of flexible (preferably silicone rubber) tubing that is connected through barbed connectors 410 to other plumbing components (such as connector 412) that can be connected into some plumbing networks similar to one shown in FIG. 26. The tubing is placed into enclosure 414 which contains a well with a ball 404. FIG. 27 shows this valve in open position when ball 404 is located above the tube 408. Slider 406 is in the right position and the slider has several linear cams (this particular valve has a cam 402) corresponding to the number of valves. Each cam can be characterized by displacement diagram where position of the slider 406 determines the state of the valve when maximum displacement corresponds to valve being completely closed while minimum displacement corresponds to open valve. The table in FIG. 26 shows an example where a certain linear position of the slider corresponds to a certain state where each of the valves is either open or closed.

FIG. 28 shows another view of mode switching pinch valve with the same valve in closed position. In this illustration, slider 406 is in the central position. In this position cam 402 pushes ball 404 into the well in enclosure 414 to its lowest position when it compresses tubing 408 and creates a closed state of this particular valve. Each of the linear cams can have its own displacement diagram corresponding to a desired algorithm of the mode switching valve.

FIG. 29 shows another cross section of the valve with four tubes correspondent to four different valves. Tubes 434 and 428 are shown in different states where cam 424 presses the ball 426 against tube 428 to close it completely while cam 430 is in a transitional state where ball 432 partially pinches tube 434 but the valve remains open. Slider 406 has a feature 420 which forms a linear slide together with rod 416 and a feature 418 on a side of the enclosure 414. In this example, rod 416 is pressed into the hole of feature 420, and when slider moves relative to the enclosure 414, the rod 416 slides relative to the corresponding holes of feature 418. Spring 422 in this configuration makes the central position of the slider a default position such that when the slider is moved in either direction and then released, it will return to the central position. Other configurations may provide special locking mechanisms keeping the slider in the desired position after it is released.

FIG. 30 shows the mode switching valve in more detail. Valve configurations may have a various number of valves with a various number of states. Combining the valves in networks can help to implement different configurations (states) where some of the valves are closed and the other are simultaneously open without the need to operate every single valve separately.

FIGS. 31-33 display a schematic of a balloon fill media control system 1100 of the present application in accordance with one or more embodiments. The system 1100 is very similar to the system 100 and therefore, like elements are numbered alike. In the system 1100, the main difference is that the vacuum relief valve 112 is disposed in a different location that is downstream of the air separator 114 (filter). More specifically, the vacuum relief valve 112 is disposed downstream of the air separator 114. The relief valve 112 shown in FIGS. 31-33 limits the differential pressure that can be generated by the volumetric pump 110. In one or more embodiments, the relief valve 112 is configured such that the pressure limit is between approximately 5 and 20 PSI, and preferably between 7 and 12 PSI. Limiting the differential pressure of the pump 110 serves a number of purposes. First, limiting the pressure developed by the pump 110 prevents excessive pressure from being developed in the balloon 102 should the user (operator) mistakenly maintain the inflate-deflate valve 108 in the "inflate" mode continuously. Another benefit of limiting the pump differential pressure is that doing so prevents the pressure in the lower chamber of the air separator 114 from exceeding the pressure at which balloon fill media may be forced through the hydrophobic membrane 116. Another reason for limiting the differential pressure that the pump 110 can generate is that this will limit the level of vacuum created by the pump 110 when the balloon 102 has been totally deflated. Limiting the amount of vacuum is important because too much vacuum applied to the balloon fill media can pull gas dissolved in the balloon fill media out of solution resulting in gas bubbles that can enter the balloon catheter 102.

As previously described, the inflate valve 108 is a valve system that has three states and is placed in one of the three states by the user. When the user is not touching the valve 108, the valve 108 automatically assumes the state shown in FIG. 31 through the action of returns springs as shown or other such mechanisms. In this state, the balloon fill media (preferably a liquid with surface tension similar to water) is circulated by the volumetric pump 110 through the balloon catheter 102. Circulating balloon fill media keeps the balloon and all parts of the catheter cool during energy delivery through the catheter 102 into the tissue. In the state shown in FIG. 31, the volume of balloon fill media contained in the system is fixed so that the balloon will maintain an inflated state with a constant volume in the balloon, while still allowing balloon fill media to circulate into and out of the balloon to perform the desired cooling function.

The air separator 114 consists of a porous hydrophobic membrane supported in a housing and dividing the housing into upper and lower chambers. When a mixture of balloon fill media and air bubbles enter the lower chamber (such a mixture is likely to been countered when balloon fill media is initially introduced into and initially dry system) the air bubbles rise to the top of the lower chamber and are forced into the upper chamber through the porous hydrophobic filter by the pressure in the lower chamber created by the pump 110. Once in the upper chamber, air exits to the atmosphere through a vent hole in the upper chamber. Balloon fill media cannot pass through the porous hydrophobic membrane because the hydrophobic nature of the membrane requires a pressure well above the operating pressure of the pump 110 to cause balloon fill media to enter the pores of the membrane. With the system configured as shown in FIG. 31, air is easily removed from the flow circuit during initial set up of the catheter 102.

The balloon catheter 102 and balloon fill media control system is supplied to the user dry. The user initially fills the balloon fill media reservoir 104 through a fill port connected to the reservoir 104. The fill port is preferably fitted with a stopcock and a sterilizing filter that serves as an added assurance that balloon fill media remains sterile as it is introduced into the balloon fill media reservoir 104. Transfer of balloon fill media from a storage vial into the reservoir 104 is usually done with the aid of a syringe 109. It will be appreciated that the fill port has been excluded from FIGS. 32 and 33 for ease of illustration.

In a preferred embodiment, the volumetric pump 110 can be a peristaltic pump and can also be called a roller pump. Such a pump 110 consists of a length of disposable elastic tubing that is installed in a durable pump head. Preferably, the durable pump head is part of the durable system used to supply the appropriate ablation energy to the catheter 102 as well as perform other functions such as displaying endoscopic images from an endoscope indwelling the ablation catheter 102 for example. The disposable elastic tubing, such as silicone rubber tubing, can then be part of a disposable balloon catheter and balloon fill media control system.

When the user places the inflate/deflate valve 108 in the position shown in FIG. 32, fluid is drawn out of the balloon fill media reservoir and is then pumped into the balloon increasing the balloon size. In this manner, the balloon can be filled to a range of continuously variable sizes in order to best match the anatomy to be ablated. When the user removes his/her hand from the actuation mechanism of the valve, the valve will return to the state shown in FIG. 31 and the balloon size to which the balloon had been inflated will be maintained by the trapped volume mode of the system.

When the user places the inflate/deflate valve 108 as shown in FIG. 33, fluid is drawn out of the balloon and is pumped into the balloon fill media reservoir decreasing the balloon size. In this manner, the balloon can be decreased in size through a continuously variable range of sizes in order to best match the anatomy to be ablated. When the user removes his/her hand from the actuation mechanism of the valve, the valve will return to the state shown in FIG. 31 and the balloon size to which the balloon has been inflated will be maintained by the trapped volume mode of the system. Alternatively, the user can hold the valve in the position shown in FIG. 33 in order to fully deflate the balloon 102. This would be done at the beginning of the procedure in order to be able to introduce the fully deflated balloon into the patient's body and at the end of the procedure to remove the balloon ablation catheter from the patient.

Burette Manifold

FIGS. 34-35 illustrate a burette manifold 1200 in accordance with one embodiment of the present invention and for use with the systems disclosed herein. The burette manifold 1200 not only contains a burette chamber (reservoir) for receiving and holding liquid but also incorporates an air separator that functions in the manner described hereinbefore with respect to other embodiments.

As one can imagine, the burette manifold 1200 includes plumbing (conduits) that allow fluid to be both delivered to the various components of the manifold 1200 and be routed therefrom. FIG. 34 is a right side perspective view of the burette manifold 1200; FIG. 35 is a close-up taken along the circle A in FIG. 34; FIG. 36 is a left side perspective view thereof; FIG. 37 is a close-up taken along the circle B in FIG. 36; and FIG. 38 is an exploded perspective view thereof.

The burette manifold 1200 can be thought of as containing a number of subassemblies. In particular, the burette manifold 1200 can be thought of as containing a burette subassembly 1210. The burette subassembly 1210 includes an elongated burette tube 1212 that has an open top end 1213 and a closed bottom end 1213. The burette tube 1212 is intended to hold balloon fill media. The burette tube 1212 can include a number of markings including an upper liquid level indicator and a lower liquid level indicator. The burette subassembly 1210 further includes a top cap 1214 that mates with the open top end 1213 and provided communication to the hollow interior of the burette tube 1212. A first tubing 1220 is provided and is routed through the top cap 1214. The first tubing 1220 can have a bent construction (e.g., L-shaped). A top cap cover 1215 covers the open top of the top cap 1214 and a hydro repellant air filter 1217 can be provided for venting air within the burette tube 1212.

The first tubing 1220 can be connected to a second tubing 1222 by means of a first connector 1223 (e.g., a double barb fitting) and a first retainer tube transition member 1225 can be coupled to the first connector 1223 and a first end of the second tubing 1222 in a surrounding manner. At the opposite second end of the second tubing 1222, a second connector 1226 (e.g., a double barb fitting) is provided and a second retainer tube transition member 1227.

The burette manifold 1200 also include an air separator or air filter subassembly 1230. The subassembly 1230 includes an upper manifold 1240 and a lower manifold 1250. The upper manifold 1240 has a top surface on which the bottom of the burette tube 1212 can rest. The upper manifold 1240 is a hollow structure and thus defines an upper (first) fluid chamber. As best shown in FIG. 37, the upper manifold 1240 includes a plurality of fluid ports, such as a first fluid port 1241, in this case a return tube connection, and a second fluid port 1243 that is formed along the same side of the upper manifold 1240. On another side, such as an opposite side, the upper manifold 1240 includes a third port 1245 that is a fill connection (FIG. 35). These fluid ports allow fluid to be delivered into the hollow interior of the upper manifold 1240.

The filter subassembly 1230 also includes a filter membrane identical or similar to the ones described herein. A filter housing 1232 is sized and configured to receive a filter membrane 1234 (e.g., a hydrophobic membrane (PTFE)). The filter membrane 1234 can have any number of different shapes and sizes.

The lower manifold 1250 is configured to mate with the upper manifold 1240 and includes a top portion that receive an O-ring 1251 that is disposed below the filter membrane 1234. The lower manifold 1230 is also a hollow structure that can receive and hold fluid. The lower manifold 1230 includes a check valve casing (housing) 1235 that receives a check valve 1237 (check valve cartridge). As shown in FIG. 37, the lower manifold 1230 also includes a fourth port 1237 that can be in the form of a supply tube connection that is formed along one side of the lower manifold 1230. Along an opposite side of the lower manifold 1230, there is a fifth port 1239.

A third tubing 1260 has a first end that is attached to the firth port 1239 and is attached at its opposite second end to the second connector 1226 and is thus attached to second tubing 1222. In this manner, the lower manifold 1230 is coupled to interior of the burette tube. A supply tube 1270 is attached to the fourth port 1237.

A fourth tubing 1280 is attached at its first end to the third port 1245 (fill connection) and is attached at its opposite second end to a valve assembly 1290. The valve assembly 1290 can be in the form of a stopcock valve assembly that comprises a stopcock valve body 1292 that has a first port that is attached to a connector 1294 (such as a female luer connector) and a second port. A syringe filter 1295 can be coupled to the second port of the stopcock valve body 1292. A male luer vented cap 1299 can be coupled to a port of the syringe filter 1295.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A balloon catheter system, comprising:
   a balloon catheter including a catheter body and an inflatable balloon coupled to
   one end thereof; and
   a fluid management system for controllably inflating and deflating the balloon, the fluid management system including:
   a reservoir for storing balloon fill media,
   a first conduit connected between the reservoir and the balloon for delivering the balloon fill media,
   a second conduit connected between the balloon and the reservoir for returning the balloon fill media from the balloon to the reservoir,
   a pump disposed along the first conduit and configured to circulate the balloon fill media along a circuit defined by the first and second conduits, and
   a valve assembly that is disposed along the first and second conduits, with the pump being disposed along the first conduit between the valve assembly and the balloon, the valve assembly being configured for placement in at least a first position, a second position, and a third position, wherein in the first position, the balloon fill media is delivered from the reservoir and pumped into the balloon for inflation thereof, wherein in the second position, the balloon fill media is drawn out of the balloon and pumped back to the reservoir, and wherein in the third position, the balloon fill media circulates from the pump through the first conduit to the balloon and through the second conduit from the balloon back to the pump and is prevented from flowing back to the reservoir from the balloon.

2. The balloon catheter system of claim 1, wherein the pump is a peristaltic pump.

3. The balloon catheter system of claim 1, wherein the fluid management system further comprises:
   an air separator configured to separate air from the balloon fill media and remove the separated air from the system, the air separator being disposed on the first conduit between the pump and the valve assembly; and
   a relief valve configured to limit differential pressure generated by the pump.

4. The balloon catheter system of claim 3, wherein the relief valve is disposed along the first conduit upstream of the air separator.

5. The balloon catheter system of claim 3, wherein the relief valve is disposed along the first conduit downstream of the air separator.

6. The balloon catheter system of claim 3, wherein the relief valve is configured to limit the differential pressure generated by the pump to between approximately 5 and 20 PSI.

7. The balloon catheter system of claim 3, wherein the relief valve is configured to limit the differential pressure generated by the pump to between approximately 7 and 12 PSI.

8. The balloon catheter system of claim 3, wherein the air separator comprises a porous hydrophobic membrane supported in a membrane housing, the membrane dividing the membrane housing into upper and lower chambers, and wherein the air separated from the balloon fill media permeates through the membrane into the upper chamber and exits the system through a vent hole in the upper chamber.

9. The balloon catheter system of claim 1, further comprising:
   a syringe configured to transfer balloon fill media from storage into the reservoir via a fill port in the reservoir.

10. The balloon catheter system of claim 1, wherein the valve assembly is a rocker valve assembly, the rocker valve assembly comprising:
    a rocker switch actuation mechanism having a first end and a second end, wherein depression of the first end places the valve assembly in the first position, wherein depression of the second end places the valve assembly in the second position, and wherein the depression of neither the first end nor the second end places the valve assembly in the third position.

11. The balloon catheter system of claim 1, wherein the valve assembly is a sliding tube valve assembly, the sliding tube valve assembly comprising:
    a valve assembly housing; and
    a sliding member disposed on a track within the valve assembly housing, wherein the sliding member is configured to move between four positions which cause the placing the valve assembly in the first position, the second position, the third position, and a fourth position, respectively.

12. The balloon catheter system of claim 11, wherein the fourth position is a sterilization position, wherein the balloon fluid media can freely pass through all conduits, and the balloon fill media is a sterilized media configured to sterilize the system.

13. The balloon catheter system of claim 11, wherein the fluid management system further comprises an illumination fiber disposed parallel to the first and second conduits, and configured to be used in conjunction with an endoscope.

14. The balloon catheter system of claim 1, further comprising:
 a burette manifold configured to hold the reservoir, the burette manifold comprising an air filter subassembly.

15. The balloon catheter system of claim 14, wherein the air filter subassembly comprises a hydrophobic filter membrane.

\* \* \* \* \*